United States Patent [19]
Widjaja et al.

[11] Patent Number: 5,577,990
[45] Date of Patent: Nov. 26, 1996

[54] TROPHOTROPIC RESPONSE METHOD

[75] Inventors: Nusa Widjaja, Brookline, Mass.;
William B. Lee, Salt Lake City, Utah;
Robert W. Fish, Lowell; Clive Bolton,
Andover, both of Mass.

[73] Assignee: Nusa Widjaja, Brookline, Mass.

[21] Appl. No.: 324,336

[22] Filed: Oct. 17, 1994

Related U.S. Application Data

[62] Division of Ser. No. 174,274, Dec. 28, 1993, Pat. No. 5,518,497.

[51] Int. Cl.$^6$ ............................................. A61M 21/00
[52] U.S. Cl. .................................................. 600/27; 600/28
[58] Field of Search .................................. 600/26–28, 745, 600/746, 731–734, 741; 128/745, 746, 731–734, 741; 331/78

[56] References Cited

U.S. PATENT DOCUMENTS

| | | | |
|---|---|---|---|
| 3,773,049 | 11/1973 | Rabichev et al. | 600/28 X |
| 3,835,833 | 9/1974 | Limoge | 600/28 X |
| 3,884,218 | 5/1975 | Monroe | 600/28 |
| 3,967,616 | 7/1976 | Ross | 600/27 |
| 4,289,121 | 9/1981 | Kupriyanovich | 600/27 |
| 4,553,534 | 11/1985 | Steigler . | |
| 4,777,937 | 10/1988 | Rush et al. | 600/27 |
| 4,892,106 | 1/1990 | Gleeson, III | 128/745 |
| 5,149,317 | 9/1992 | Robinson | 600/27 |
| 5,259,830 | 11/1993 | Masuda | 600/27 |
| 5,306,228 | 4/1994 | Rubins | 600/27 |

FOREIGN PATENT DOCUMENTS

| | | | |
|---|---|---|---|
| 1422959 | 1/1976 | United Kingdom | 600/27 |

OTHER PUBLICATIONS

Gordon E. Carlson, *Signal and Linear System Analysis.*, 1992, Chapter 2 pp. 42–66.

*Primary Examiner*—Lee S. Cohen
*Assistant Examiner*—Herman J. Robinson
*Attorney, Agent, or Firm*—Weingarten, Schurgin, Gagnebin & Hayes LLP

[57] ABSTRACT

A trophotropic response system which aids a user in achieving a relaxation response. In one embodiment the system includes a control unit and an audio-visual unit. The control unit includes a processor and associated hardware and software to control the audio-visual unit. The audio-visual unit includes a light producing unit having a pair of earphones coupled thereto. The light producing unit includes a plurality of light sources which direct light toward a diffuser screen disposed between the eyes of a user and the light sources. This arrangement permits the user to see light from the light sources diffused over a large visual angle. The light sources produce light and the earphones produce sound in response to audio and light control signals provided by the processor of the control unit. The signal characteristics of the light and sound control signals may be varied within predefined limits to aid the user in performing a relaxation exercise.

11 Claims, 19 Drawing Sheets

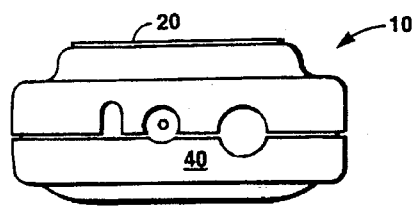
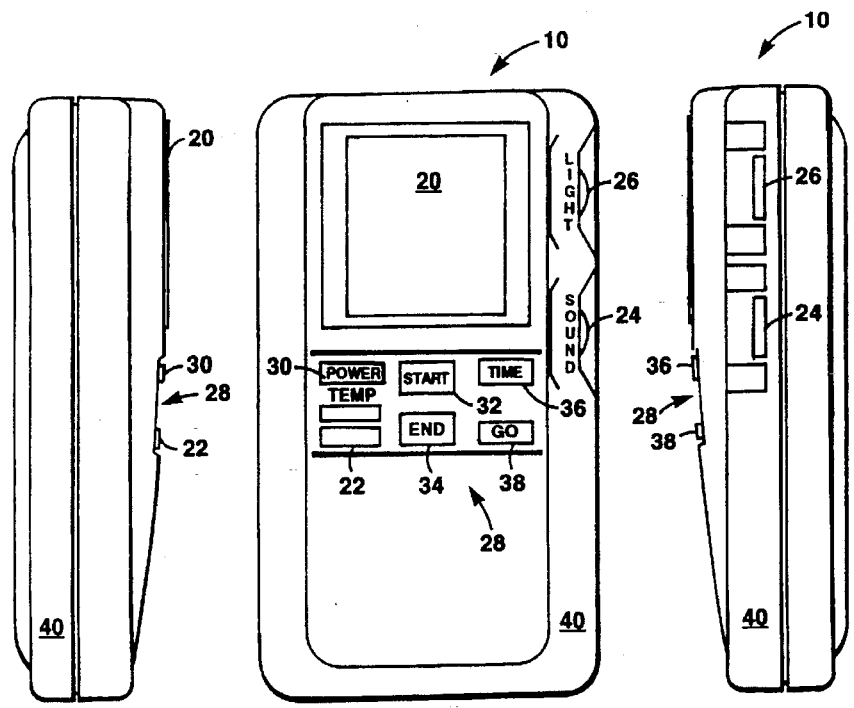
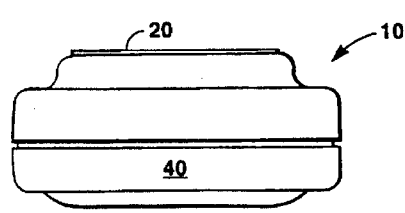
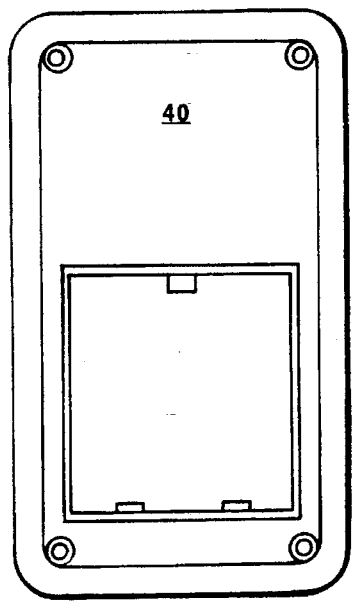

TROPHOTROPIC RESPONSE METHOD

This application is a division of application Ser. No. 08/174,274 filed Dec. 28, 1993 now U.S. Pat. No. 5,518,497.

FIELD OF THE INVENTION

The invention relates to apparatus and methods of relaxation in general and audio-visual devices for providing an environment conducive to elicitation of a relaxation response in particular.

BACKGROUND OF THE INVENTION

In the presence of stress, the autonomic nervous system of a human body causes a variety of physiological changes in the human body. Such changes may include, for example, an increase in heart rate and respiration rate, suppression of digestive activity, tensing of muscles and constriction of blood vessels. These physiological changes in response to stress are collectively referred to as the ergotrophic response or the "fight or flight" response. This response has evolved in humans in order to prepare the body for self-protection in the face of a physical threat.

In modern society, however, most sources of stress are not the result of impending physical danger but rather result from the continual exposure to daily stressors, such as deadlines and commitments. As a result of the continuous exposure to such stressors, the body is subjected to undue strain resulting in a decrease in performance.

To reduce this ergotrophic response, it is necessary to cause the body to relax or undergo a trophotropic or relaxation response. A body undergoing a trophotropic response reduces its heart and respiration rate, relaxes its muscles, and dilates its blood vessels thereby resulting in a lowering of its blood pressure. In this relaxed state, the cognitive efficiency of the person is increased.

In recent years relaxation techniques such as meditation, yoga, autogenic training and electronic biofeedback devices have aided individuals in achieving the relaxation response. Each of these techniques has attributes and deficiencies associated with it, and so, has its adherents and its detractors. The present invention relates to a device which aids the user in obtaining the relaxation response.

SUMMARY OF THE INVENTION

A trophotropic response system includes a control module for providing a visual signal and an aural signal having an ocean signal component and a binaural beat signal component. The trophotropic response system further includes an audio unit for receiving the aural signal from the control module and a visual unit for receiving the visual signal from the control module wherein the visual signal is provided having a frequency corresponding to the frequency of the binaural beat component of the aural signal. With this particular arrangement a trophotropic response system for aiding a user in obtaining a relaxation response is provided. The audio unit and visual unit may be coupled to a frame and provided as an integral part thereof. The control module may include a microcomputer subsystem for providing the visual signal and the aural signal, a display driver coupled to said microcomputer subsystem and a display, coupled to the display driver, for displaying information provided from the microcomputer system. The visual unit may include a visor having first and second opposing surfaces, coupled to the frame and a diffuser screen, having first and second opposing surfaces, wherein the diffuser screen is also coupled to the frame and arranged such that a first surface thereof is disposed proximate a first surface of the visor. At least one light source may be coupled to the visor and disposed to project light onto the diffuser screen. In a preferred embodiment, the light source may include a plurality of light sources each of which are disposed between the visor and the diffuser screen and which project light onto the diffuser screen. The light sources may be provided for example as light emitting diodes which may emit either a single color light or a plurality of different colors of light. The aural signal may include a pair of binaural beat signal components each having a sinusoidal characteristic. A first binaural beat signal component having a frequency in a first frequency range may be provided on a left channel of the audio unit and a second binaural beat signal component having a varying frequency equal to the left channel frequency plus the binaural beat frequency may be provided on a right channel of the audio unit. The ocean signal component of the aural signal may correspond to pink noise modulated by a pair of envelope signals wherein the pink noise in each channel is generated separately but is provided having the same amplitude. Pink noise is a particular spectrum of noise in which high frequency components are reduced in amplitude and low frequency components are increased in amplitude in a linear ramp. It should be noted that other types of noise may of course also be used. The visual signal may be provided from a sinusoidal signal and a rectangular wave signal. The sinusoidal signal may be provided having a first predetermined frequency and the rectangular wave signal may be provided having a predetermined duty cycle wherein the duty cycle of the rectangular wave signal increases linearly from a first duty cycle at a first predetermined frequency to a second different duty cycle corresponding to the predetermined duty cycle at a second predetermined frequency.

BRIEF DESCRIPTION OF THE DRAWING

FIG. 1 is a plan view of an embodiment of the control module of the invention;

FIG. 2 is a right side view of the embodiment of the control module of the invention of FIG. 1;

FIG. 3 is a left side view of the embodiment of the control module of the invention of FIG. 1;

FIG. 4 is a back view of the embodiment of the control module of the invention of FIG. 1;

FIG. 5 is a front view of the embodiment of the control module of the invention of FIG. 1;

FIG. 6 is a bottom view of the embodiment of the control module of the invention of FIG. 1;

DESCRIPTION OF THE PREFERRED EMBODIMENT

Figure 7:
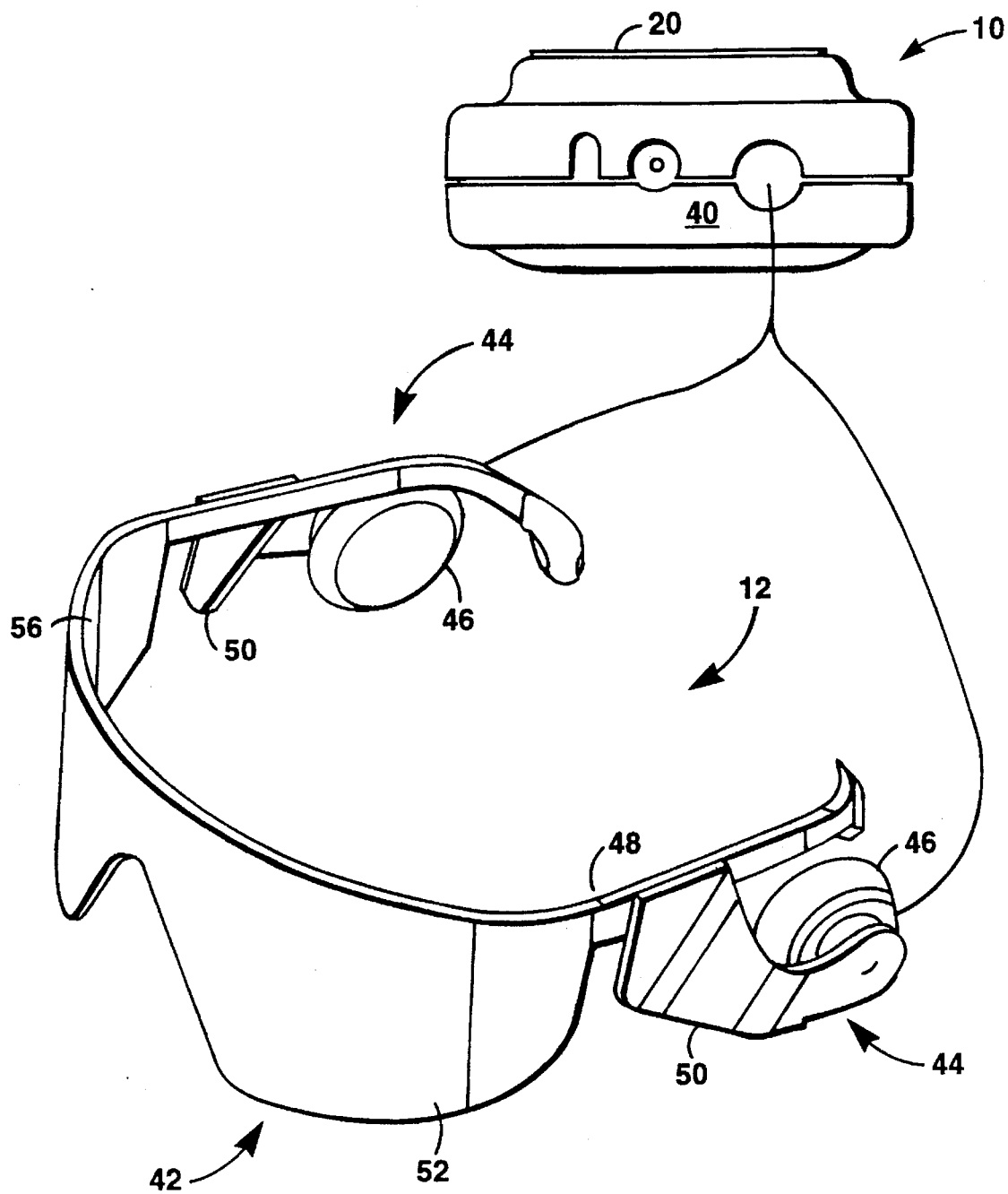
FIG. 7 is a perspective view of an embodiment of the audio-visual module of the invention.

Referring now to FIGS. 1–7 and in brief overview, a trophotropic response system 9 includes a control module 10 (FIGS. 1–6) and an audio-visual module 12 (FIG. 7). Control module 10 is coupled to audio-visual 12 via a cable 13. The control module 10, in one embodiment, includes a liquid crystal display (LCD) 20, a temperature sensor 22 and a series of controls, including a sound intensity control 24, a light intensity control 26, and a keypad 28. The keypad 28 includes a series of buttons used to control the functioning of the system. These buttons include a POWER (on/off) button 30, a START button 32, an END button 34, a TIME button 36 and an initiate or GO button 38. The function of each of the controls will be described in detail below. The liquid crystal display 20, keypad 28 and controls 24, 26 are incorporated into a resilient plastic housing 40 which also incorporates the electronics and power supply for the system 9.

The liquid crystal display 20 is here provided as a 79 segment custom display that is used to display vertical bar graphs of: the starting frequency of the light and sound generated by the audio-visual unit 12, the ending frequency of the light and sound generated by the audio-visual module 12, the time duration of the session, and the finger temperature of a user. Three additional segments are used to indicate low battery conditions, manual mode, and "AFR" mode. Those of ordinary skill in the art will now recognize of course that other information may also be displayed. For example, display 20 may display any of the physiological indications such as heart rate, muscle tension, brainwave, skin conductants, heart rate or any other physiological indicator known to one of ordinary skill in the art.

The audio-visual module 12 (FIGS. 7 and 8–8B) in one embodiment is provided as a set of goggles having a video unit 42 and an audio unit 44. The audio unit 44 includes a set of stereo-earphones 46 each of which is attached to the frame 48 of the goggles by an adjustable mounting arm 50. Mounting arm 50 may be moved back forth along frame 48 to adjust to the size of the users head. A first end of cable 13 may be coupled to control module 10 via a so-called MICRO-DIN connector. A second end of cable 13 is bifurcated. Each bifurcated cable section is coupled to a corresponding one of the stereo earphones 46 The video unit 42 is constructed as an opaque visor 52 upon which are disposed a plurality of light sources 54. The light sources 54 are here provided as light emitting diode (LEDs) lamps 54a–54d, disposed over a first surface of and toward the edges of the visor 52. Although four LEDs are here shown, it may, in some applications, be advantageous to use fewer than four or more than four light sources. The particular number of light sources may be selected according to a variety of factors including but not limited to the environment which is to be provided to the user. Thus while audio visual module 12 may include only a single light source preferred embodiments use at least two light sources per eye.

In the case where only a single LED is used the LED may appear as a point source to a user. Thus to minimize the appearance of the light source as a point source, an additional layer in the diffusion screen may be required.

It should be noted that light sources 54 may be positioned along any portion of visor 52. If LEDs 54 are spaced a relatively large distance from the center of visor 52, it is possible to position the LEDs such that an environment is provided for only one side of the brain. Thus, if LEDs 54 were disposed close to the temple 50 and only one pair of LEDs were periodically illuminated then the opposite side of the brain on which the LEDs were excited will be subject to the environment provided by the system 12.

It should be also noted however, that an increase in the number of light sources 54 which are disposed on visor 52 provides a concomitant increase in the color variations which may be provided through the LEDs and also provides a greater flexibility in the positioning of particular ones of the LEDs. That is, the LEDs may be disposed in different locations and provide a different light field to the user. Furthermore, light sources 54 need not be provided as light emitting diodes but could also be provided from fiber optic rods, for example, fed through the goggles and disposed to emit light as desired. Here, LEDs 54 project light onto a diffuser screen 56 having a generally translucent appearance and a thickness typically of about 0.5 mm. Diffuser screen 56 may be provided for example from calendered LEXAN and is positioned between the LEDs 54 and the eyes of the user. A polyester foam spacer 53 having a thickness typically of about 0.375 inch separates diffuser screen 56 from visor 52. Spacer 53 provides clearance between the visor 52 and the diffuser screen 56 for the LEDs 54. The thickness of spacer 53 should be selected such that the light emitted from LEDs 54 is properly diffused by the diffusion screen. That is, the light is diffused by diffusion screen 56 such that substantially no point sources of light are visible to a user.

LEDs 54 in the present embodiment are provided as red-light emitting Gallium Astatime Arsenide (GaAtAs) super-luminosity LED lamps manufactured by Sharp Electronics. Other types of LEDs may also be used. For example, Gallium Aluminum Arcinide (GaAlAs) LEDs which are very efficient in terms of brightness may also be used. It should be noted that the LEDs 54 should provide a relatively bright light and should be responsive to signals fed thereto. Consequently GaAlAs LEDs may be particularly useful in the present invention since they generally provide a relatively bright light for a particular LED size. Thus, in this particular embodiment it is desirable to use LEDs which provide a relatively bright light in a relatively small package size.

It should also be noted that LEDs 54a–54d may be provided as multicolor LEDs which emit a plurality of different color light or even a continuous range of colors within a predetermined band of the visible light spectrum. Moreover, in some embodiments it may be desirable to use a two color LED of the type manufactured by SHARP and identified as part number GL3UR8. Other commercially available LED lamps having similar package sizes and electrical characteristics may also be used.

Diffuser screen 56 diffuses the light emitted from the LEDs 54 over a large visual angle. The diffuser screen 56 is provided having a thickness typically in the range of about 0.010 inch to 0.015 inch and may be provided for example from a translucent plastic material. An inner polyester foam pad 58 having a thickness typically of about 0.25 inches is located along the inner top surface of the diffuser screen 56 to provide a padded surface to rest against the forehead of the user.

The LED's 54 and earphones 46 produce light and sound, respectively, in response to signals fed thereto from control module 10. By adjusting the sound intensity 24 and light intensity 26 controls of the control module 10, the intensity of the light from the LEDs 54 and the volume of the sound produced by the earphones 46, respectively, may be varied to suit the individual user.

It should also be noted that in some embodiments a sensor for measuring a physiological characteristic of a user, may be disposed on the goggles such that the sensor contacts a predetermined region of the user. For example, such a sensor may contact a portion of the users head such as the user's face. In addition to a temperature sensor, the sensor may be provided as any type of sensor including but not limited to a muscle tension sensor, a heart rate sensor, an electro dermal resistance (EDR) sensor or an EMG sensor.

In general, the audio signal generated by the earphones 46 has a pink noise or "ocean" background component and a binaural beat component. The binaural beat component of the sound may be generated by providing an audio signal having a first frequency, for example 100 Hz in a first one of the earphones 46, and providing an audio signal having in the other earphone 46 a second frequency equal to the first frequency plus the binaural beat frequency. Thus, as the binaural beat frequency is changed, the frequency of the audio signal in the second earphone 46 changes accordingly.

The ocean sound component is provided as a stereo signal and provides the user with a sensation of motions in the left to right and front to back directions. Thus, the ocean signal component closely emulates the sound provided by the actual ocean.

The ocean signal component is generated via the microprocessor as will be described further below in conjunction with FIGS. 14–14D. Furthermore, the ocean sound component may be synchronized with other stimulus provided to the user including the light signals from light sources 54 and the binaural beat frequency signals. Thus, when the light source emits light at a frequency in the beta frequency range typically of about 20 Hz the frequency of the ocean sound has a corresponding increase. However, when the frequency of the light signal is in the alpha frequency range for example, the frequency of the ocean signal component is reduced. Thus, the system provides an optimum environment in aiding the user to achieve the trophotropic response.

The starting binaural beat frequency may be set by the user by pressing the START button 32 (FIG. 1) repeatedly until the desired starting binaural beat frequency is displayed on the LCD display 20. The ending binaural beat frequency may similarly be set by pressing the END button 34 (FIG. 1) repeatedly. Similarly, by pressing the TIME button 36 (FIG. 1) the user can manually select the time duration of the session. Trophotropic response system 9 may then record the temperature of the user if the user places their finger on the temperature sensor 22.

The user then positions the audio-visual module 12 such that the user's senses of sight and sound are subject to the visual and audio signals provided by the system 9 after the user presses the GO button 38 (FIG. 1). Typically, after the user pushes the GO button 38, the user hears the starting binaural beat frequency sound imposed upon pink background noise. The binaural beat frequency is then decreased at a rate of 2.4 Hz/minute, in steps of 0.1 Hz until the ending binaural frequency as set by the user is reached. Once this frequency is reached, this binaural beat frequency is maintained for the remainder of the session. During the session the LEDs 54 emit light having a frequency and intensity related to the binaural beat frequency. For example, the LEDs 54 may flash at a frequency equal to and in coincidence with the binaural_beat frequency. The binaural beat frequency may be decreased at a rate typically in the range of about 2.0 Hz/minute to 3.7 Hz/minute That is predetermined values may be included in the software such that the rate of change of frequency is different from 2.4 Hz/min, or that the step is different from 0.1 Hz. Each user may prefer a slightly different rate change. Like wise, the step frequency of 0.1 Hz may typically be varied by about +25 percent. However an optimum rate change is typically about 2.4 Hz/minute.

As the session ends, the intensity of the light signal emitted from the LEDs 54 and the intensity of the sound signal provided to the earphones 46 is gradually reduced (i.e. is faded out). At the end of the session, the user can again have the system measure finger temperature by placing their finger on the temperature sensor 22. A change in temperature detected by the temperature sensor 22 may be indicative of a change in blood circulation and thus may provide an indication of how well the user has achieved the relaxation response. For example, an increase in temperature may indicate the user has achieved a relaxation response. It should be noted that the system may operate in a so-called pre-programmed mode or in a so-called manual mode. In both the pre-programmed and manual modes, the user may select the starting frequency and the ending frequency.

Furthermore, in the manual mode the user may update the frequency settings during the session. The system thus allows a user to select the type of session to be run.

For example, the user may simply press the GO button and the system executes a session for a predetermined period of time (e.g. 15 minutes) with predetermined start and end frequencies. Alternatively, the user may measure the start and end finger temperatures then go to manual mode and select the start and end frequencies and then begin execution of the session by pressing the GO button. Alternatively, the user may select a mode wherein the user sets the time, presses GO and then is able to manually set the start and end frequencies.

The functionality described above is controlled by a series of electronic components which, in this embodiment, are disposed primarily within the resilient plastic housing 40. Those of ordinary skill in the art will recognize, of course that the placement of any or all of such electronic components is arbitrary and that all or a portion of the electronics may be disposed in the audio-visual headset 12, for example.

Figure 9:
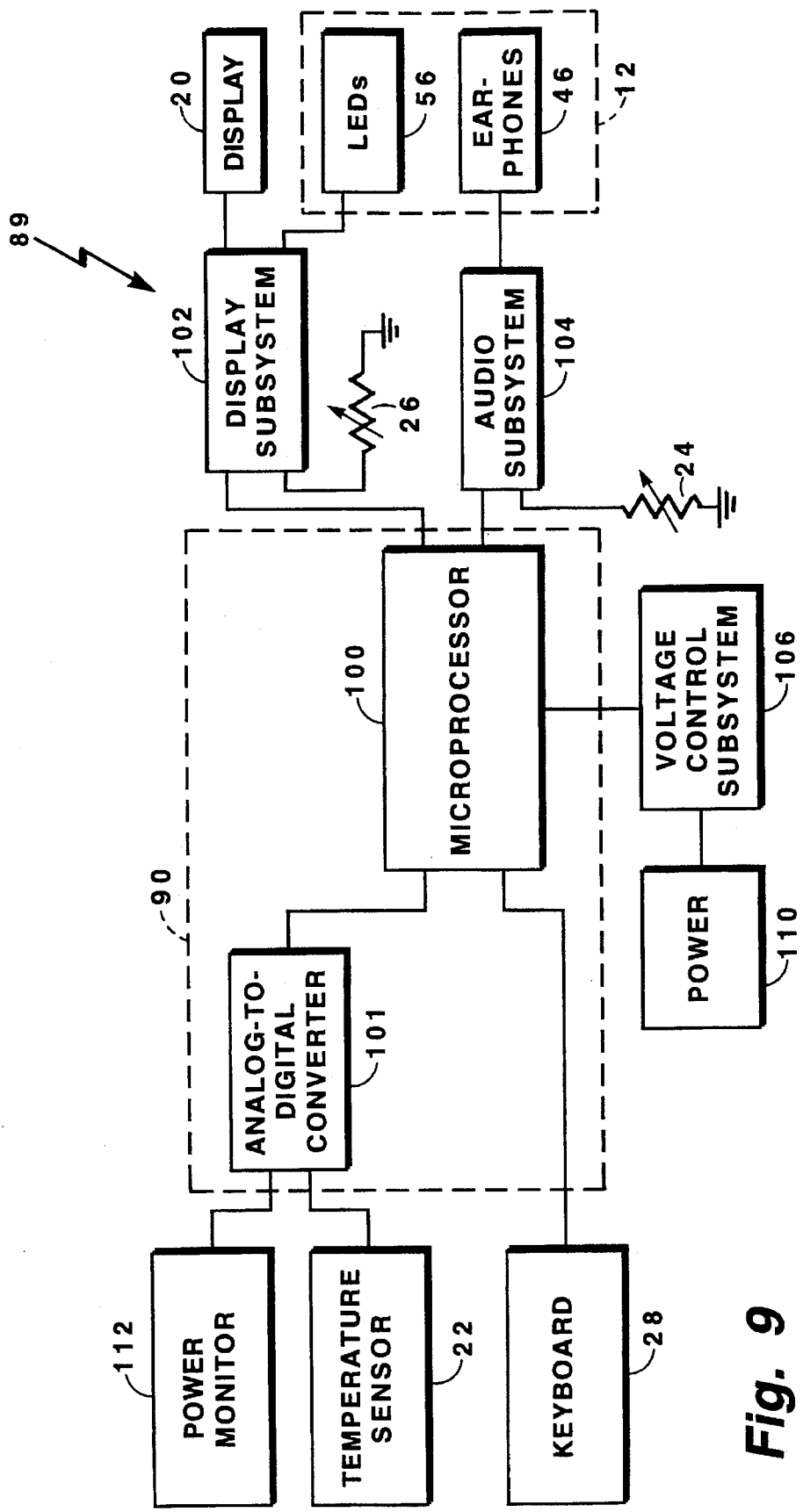
FIG. 9 is a block diagram of an embodiment of the system of the invention.

Referring now to FIG. 9, a block diagram of an embodiment of the electronic components 89 of the system of the invention is shown. In this embodiment, system electronics 89 includes a microcomputer subsystem 90 which receives its instructions from the keypad 28 of the control module 10. In the embodiment shown, the microcomputer subsystem 90 includes a microprocessor 100 and an analog-to-digital converter (ADC) 101. The microcomputer subsystem 90 transmits data and control signals to the liquid crystal display 20 and LEDs 54 through a display subsystem 102. The light intensity of the LEDs 54 is jointly controlled by both the microprocessor 100 and the light intensity control 26.

Similarly the microcomputer 90 transmits audio and control signals to the earphones 46 of the audio-visual module 12 through an audio subsystem 104 which includes an amplifier/mixer arrangement. The gain of the audio subsystem 104 is determined by a variable resistor 24. The resistance of the resistor 24 may be adjusted to provide a means for controlling the sound level of audio signals fed to the earphone 46.

Power to the system is provided by battery or external power source 110 and is regulated by voltage control subsystem 106.

The microprocessor 100 receives user temperature data from the temperature sensor 22 by way of the analog-to-digital converter 101 portion of the microcomputer subsystem 90. Upon the user's placing of his or her finger on the temperature sensor 22, the analog data converted by the ADC 101 is supplied to the microprocessor 100 for analysis. The ADC 101 also provides data to the microprocessor 100 from the power monitor subsystem 112.

Figure 10:
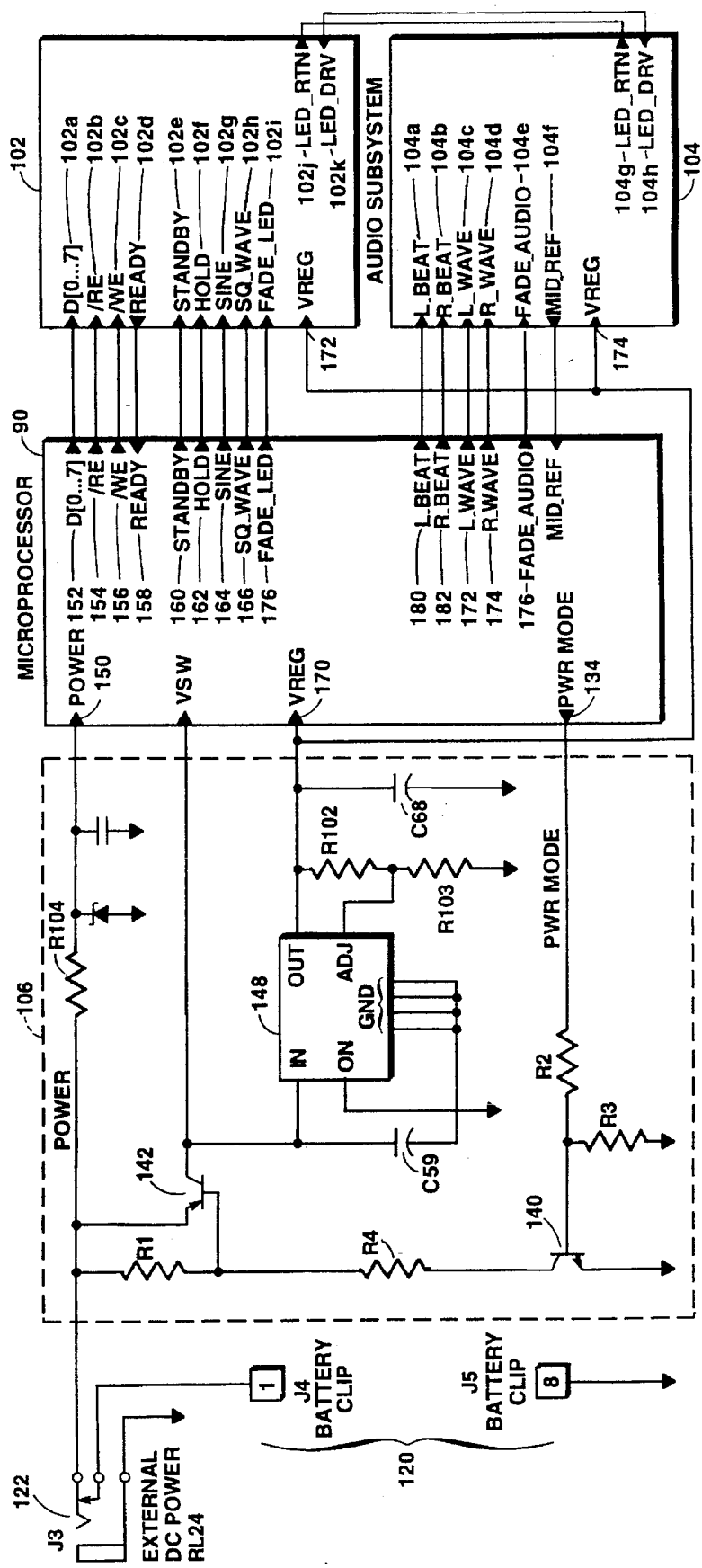
FIG. 10 is a circuit level functional diagram of the embodiment of the system of FIG. 9.

Referring now to FIG. 10, portions of the microcomputer subsystem 90, display subsystem 102, the audio amplifier/mixer 104 and the voltage control subsystem 106 are shown in more detail. The trophotropic response system 9 receives power 110 from either a battery connection 120 or an external DC power jack 122. The power supply 110 provides power to the microcomputer subsystem 90 through both a power input terminal 110 and a regulated voltage input terminal VREG 130. A POWER input terminal 150 of microprocessor 90 is coupled directly to the power supply 110 (FIG. 9) through voltage control subsystem 106. A voltage regulator 148 disposed in voltage control subsystem 106 provides a regulated voltage to the VREG input terminal 170 of the microcomputer subsystem 90, the VREG input terminal 172 of display subsystem 102 and the VREG input terminal 174 of the audio subsystem 104.

The system 9 may operate in either a lower power consumption mode or in an on mode. In the low power consumption or "sleep-mode" only the microcomputer subsystem 90 is supplied power. In the "on mode" a regulated voltage is provided to the entire system 9. The power mode in use is controlled by a signal line 134 of a parallel output port which is designated as the power mode (PWR_MODE) output terminal of microcomputer subsystem 90.

A voltage low signal on the PWR_MODE output terminal 134 of the microprocessor subsystem 90 causes an NPN transistor 140 to turn off, thereby turning off a PNP transistor 142. The turning off of PNP transistor 142 turns off the input power to the system voltage regulator 148, permitting the system to enter the power conservation or sleep mode. The directly applied, unregulated, power to the POWER input terminal 150 of microcomputer 90 permits microprocessor 100 (FIB. 9) of the microcomputer subsystem 90 to function thereby permitting the system 9 to operate when a user enters data from the keypad 28 (FIG. 1).

Thus, in sleep mode the microcontroller remains powered, in a power conserving state. Once the system enters sleep mode, the only key that will cause the microcontroller to respond is the POWER key 30 (FIG. 1). Once the POWER key is pressed, the microcontroller emerges from sleep mode and can then accept commands from the user input through keypad 28 (FIG. 1).

Video data for the LCD display 20 is supplied to the display subsystem 102 by the microcomputer subsystem 90 through an 8 bit parallel port 152. Display subsystem 102 is coupled to a second 8 bit parallel port of the microcomputer subsystem 90. The second 8 bit parallel port includes lines 154–162 which function to provide read enable (/RE) 154, write enable (/WE) 156, READY 158, and STANDBY 160 signals to the display subsystem 102 and control the updating of the LCD display 20.

Additionally, and as will be described in detail in conjunction with FIG. 11 below, a signal having a sinusoidal shape is fed from SINE line 164 of the second parallel port to terminal 102g of display subsystem 102. Similarly microcomputer subsystem 90 generates a square wave signal SQ_WAVE at terminal 166, which is fed to terminal 102h of subsystem 102.

Likewise, and as also will be described further below, the microcomputer subsystem 90 generates at a third parallel output port a pair of audio signals designated L_WAVE and R_WAVE on signal lines 172, 174. The left wave (L_WAVE) and right wave (R_WAVE) signals are coupled from terminals 172, 174 of microprocessor 90 to the audio amplifier/mixer subsystem 104 at terminals 104a, 104b. A FADE signal is coupled from microcomputer to both display subsystem 102 and the audio amplifier/mixer subsystem 104.

Signals from two terminals of the microcomputer subsystem 90 are processed to generate the left beat (L_BEAT) 180 and right beat (R_BEAT) 182 signals for the audio mixer/amplifier subsystem 104. The functions of each of these signals are further described below.

Figure 11:
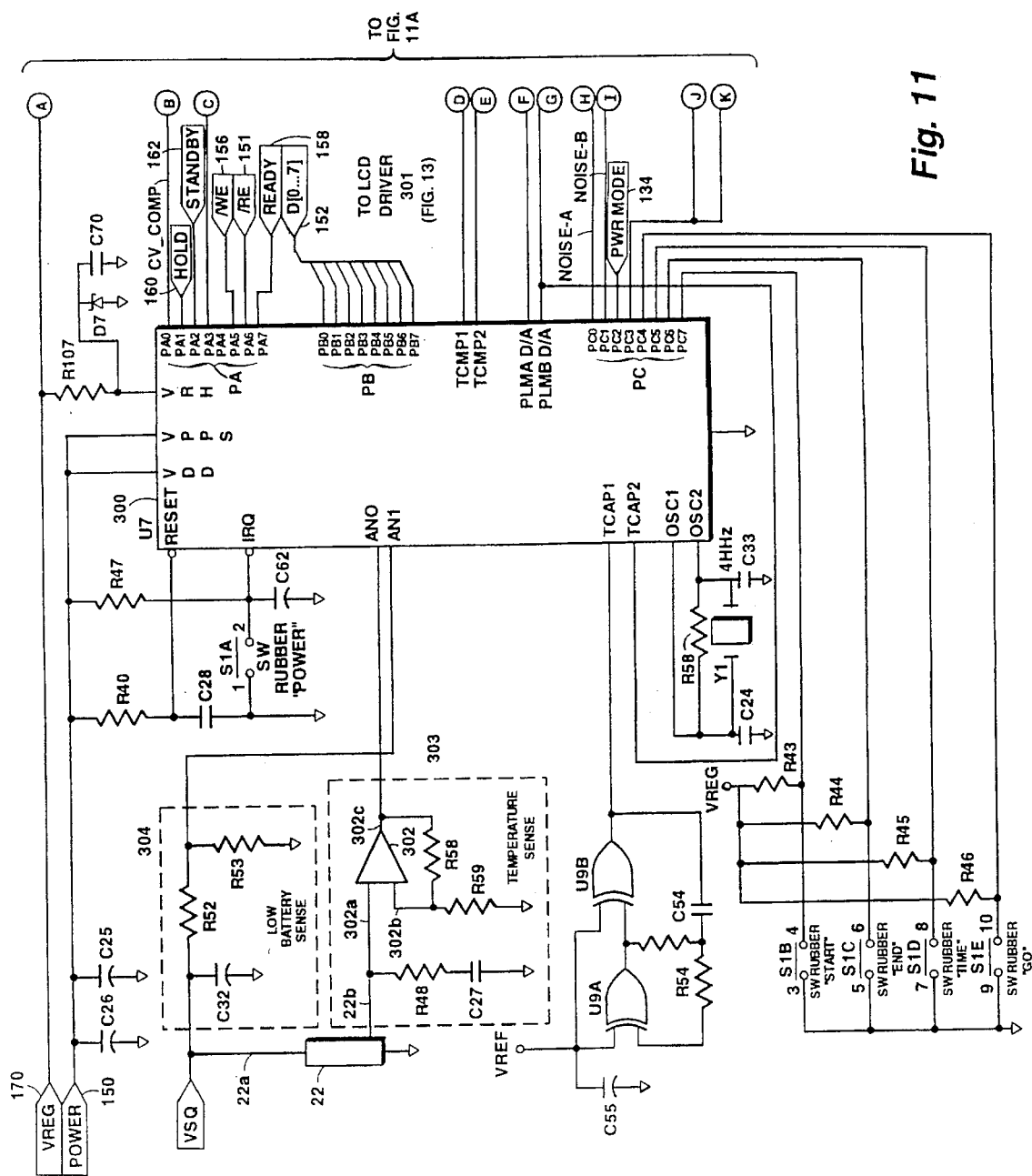
FIGS. 11–11A are a schematic diagram of the microprocessor portion of an embodiment of the system of FIG. 9.

Referring now to FIG. 11. in which like elements of FIG. 10 are provided having like reference designations, FIG. 11 depicts the microcomputer subsystem 90 in more detail. Microcomputer system 90 includes a micro-controller 300 which may be provided, for example, as the type manufactured by Motorola Corp. and identified as part number 68HC05B4-PLC. Those of ordinary skill in the art will recognize of course that any micro-controller having similar operating features and characteristics may also be used.

Microcontroller 300 receives power and a regulated voltage from lines 110, 150 respectively as described in conjunction with FIG. 10 above. Microcontroller 300 includes microprocessor 100 (FIG. 9) A/D converter 101 (FIG. 9), and a plurality of parallel input/output (I/O) ports PA, PB and PC. Each of the I/O ports include a plurality of I/O terminals respectively designated PA0-PC7.

Touch sensor 22, described above in conjunction with FIGS. 1–9, has an input terminal 22a coupled to input voltage terminal VSW and an output terminal 22b coupled through a temperature sense circuit 303 to a temperature sense input terminal AN0 of microcontroller 300. At predetermined times the controller executes a temperature routine. During the temperature routine, the LCD is updated with the A/D information from temperature sensor 22. Temperature sense circuit 303 includes an amplifier 302 having a first input port 302a coupled to sensor 22. An amplifier output port 302c is coupled to microcontroller temperature sense input terminal AN0. A resistor R68 provides a feedback signal path between amplifier output port 302c and a second amplifier input port 302b. Thus amplifier 302 provides a signal to temperature sense input terminal AN0 of microcontroller 300.

Input voltage terminal VSW is also coupled through a battery sense circuit 304 to a battery sense input terminal AN1 of microcontroller 300. The battery voltage is checked once before each session. If the battery voltage is low, an indication is provided on the LCD display. Battery sense circuit 304 is here provided from a capacitor C32 having a first electrode coupled to the voltage input terminal and a second electrode coupled to ground and resistors R52, R53 coupled as shown. Thus via temperature sensor 22 and battery sense circuit 302, microcontroller 300 monitors both the battery voltage and user temperature and, as described above in conjunction with FIGS. 9 and 10, performs appropriate functions and provides signals in response to temperature and battery sense signals fed thereto.

The microcontroller 300 includes a pair of output signal lines PLMA, PLMB. Each of the output signal lines are coupled to corresponding ones of a pair of amplifiers 306, 308 at respective input ports 306a, 308a. Amplifiers, 306D, 308C have respective output ports 306C, 308c coupled to a first electrode of respective ones of a pair of transistor Q5, Q7. Each of the amplifiers 306D, 308C are also provided having negative feedback between the respective output ports 306C, 308C and second input ports 306b, 308b.

Microcontroller 300 controls the signal level of each of the audio signals L_WAVE, R_WAVE via the signal levels of signals fed from the pair of control lines PLMA, PLMB to the amplifiers 306, 308. Thus, control line PLMA provides a signal to input port 306a of amplifier 306D. Amplifier 306 in turn provides an output signal at output port 306d which drives the emitter electrode of the transistor Q7 to provide an output signal having a predetermined signal level at the output port 172.

Likewise, control line PLMB provides a signal to the amplifier 308 which drives the emitter electrode of the transistor Q6 to provide an output signal having a predetermined signal level at the output port 174. Thus, the microcomputer system 90 provides a pair of audio output signals L_WAVE and R_WAVE at respective output terminals 172, 174.

Microcontroller 300 includes a pair of time compare registers having output ports TCMP1, TCMP2 on which a pair of beat signals L_BEAT, R_BEAT are provided to output ports 180, 182 through respective ones of filters 307, 309. The L_BEAT and R_BEAT signals are provided from microcontroller 300 as a series of signal pulses. The series of pulse signals generally resemble a square wave signal. Square wave signals are a composite of sinusoidal shaped signals at a base frequency and higher frequencies. Here, only the base frequency signal is desired. Thus filters 307, 309 are here provided having a low pass filter characteristic. By feeding the L_BEAT and R_BEAT signals through low pass filters 307, 309, substantially all of the higher frequency signals are removed and only the base frequency signal remains. Furthermore, filters 307, 309 filter out relatively high frequency noise spikes which may occur in the signal path and thus prevent such noise spikes from being fed to output ports 180, 182.

To provided the signals L_BEAT and R_BEAT, the time compare register are loaded with a value from the processor of microcontroller 300 and the time compare registers begin to countdown. When the countdown is complete the output toggles (e.g. 1 to 0 or 0 to 1) and the countdown starts again. In TTL logic this corresponds to a pulse train signal having voltage levels of substantially 0 volts and substantially five volts. Other voltages corresponding to different logic types may of course also be used. Thus, the L_BEAT, R_BEAT signals are output on respective ones of ports TCMP1, TCMP2 of microcontroller 300 and are provided having alternate values of 0 and 1.

Output ports TCMP1, TCMP2 are also coupled to a pair of input ports 310a, 310b of an exclusive-or (XOR) logic circuit 310. XOR logic circuit 310 receives the input signals fed thereto on input ports 310a, 310b and provides an output signal having a sinusoidal shape at output port 310c.

Output port 310c of the XOR logic circuit 310 is coupled to output terminal 164 through a filter 311 having a low pass filter characteristic. Logic circuit 310 provides a sinusoidal output signal SINE to terminal 164 and also provides a high impedance characteristic at terminal 164.

Microcontroller 300 also provides a control voltage compare signal CV_COMP from terminal PA0 of I/O port PA to a first terminal of an RC circuit 313. A second terminal of circuit 313 is coupled to an amplifier 314 at a first input port 314a. A second input port 314b of amplifier 314 is coupled to terminal 164 to thus couple a portion of the signal provided by logic circuit 310 to the first amplifier input port. When the amplitude of the signal provided by microcontroller 300 is greater than the amplitude of the signal at input port 314a, amplifier 314 provides an output signal at output port 314c having a first signal level. However, when the amplitude of the signal provided by microcontroller 300 to input port 314a is less than the amplitude of the signal at input port 314b, amplifier 314 provides an output signal having a second different signal level. Thus, amplifier 314 provides an output signal SQUARE having a square waveform shape at output terminal 166.

The control voltage compare signal CV_COMP fed through the RC circuit 313 functions in the manner of a pulse width modulator. The signal provided at the second terminal of the RC circuit is provided having an average DC voltage level corresponding to the amplitude and duration of the CV_COMP signal. Thus the CV_COMP signal provides a threshold voltage to the comparator circuit 314 at input terminal 314a.

When the sign wave coupled to the second input port 314b of the comparator circuit 314 has a voltage level which is less then the voltage level of signal CV_COMP, comparator circuit 314 provides a "low" output signal. However, when the sign wave signal coupled to comparator input port 314b has a voltage level which is greater than the voltage level of threshold voltage at comparator input terminal 314a, the output of the comparator circuit is "high." Thus, the comparator circuit 314 provides a square wave signal SQUARE at output terminal 314c. The frequency and amplitude of the SQUARE wave signal is dependent upon the signals CV_COMP and SINE.

Microcontroller 300 provides another output signal at A terminal PC3 of I/O port PC. The output signal is coupled from terminal PC3 through a pair of resistive branch arms to a control electrode Q9A of a transistor Q9. The first branch arm includes a resistor R51 and a diode D4 coupled in series between terminal PC3 and the control electrode Q9a. The second branch arm includes a resistor R50 connected in series between terminal PC3 and the control electrode Q9a.

A control signal provided from microcomputer output port PC3 controls the start-up, ramp-up and the ending fade-out of LEDs 54 and the audio signal. A resistor R51 is serially coupled between port PC3 and an anode of a diode D4. A cathode of diode D4 is coupled to a first electrode of an electrolytic capacitor C29. A resistor R50 is coupled in parallel with resistor R51 and diode D4. A transistor Q9 has a first electrode Q9a coupled to the junction of the diode cathode, resistor R50 and capacitor C29.

Transistor Q9 has a second electrode Q9b coupled to a first reference potential VREG and a third electrode Q9c coupled to a first electrode of a variable resistor R100. A second electrode of resistor R100 is coupled to a second reference potential, here corresponding to ground. A third electrode of register R100 is coupled to an output terminal 176. Output signal FADE_LED is coupled from transistor electrode Q9c to the output terminal 175. Output signal FADE_AUDIO is coupled from the third terminal of resistor 100 to output terminal 76.

The resistance value of resistor R51 and D4 limit the current flow into electrolytic capacitor C29 and thus establish a time period during which capacitor C29 is charged to a predetermined level. The resistance value of resistor R50 establishes a decay time by regulating the rate at which capacitor C29 discharges. Transistor Q9 provides signal current gain. Transistor emitter Q9b is coupled to variable resistor R100. The resistance value of resistor R100 may be changed which provides a corresponding change in the value of the FADE_AUDIO signal.

The FADE_AUDIO signal controls the amplitude of the sound emitted by earphones 46 (FIGS. 7, 8–8B) such that the sound provided by earphones 46 may be gradually increased or reduced (i.e. faded in or faded out) rather than simply being abruptly turned on or off.

Figure 12:
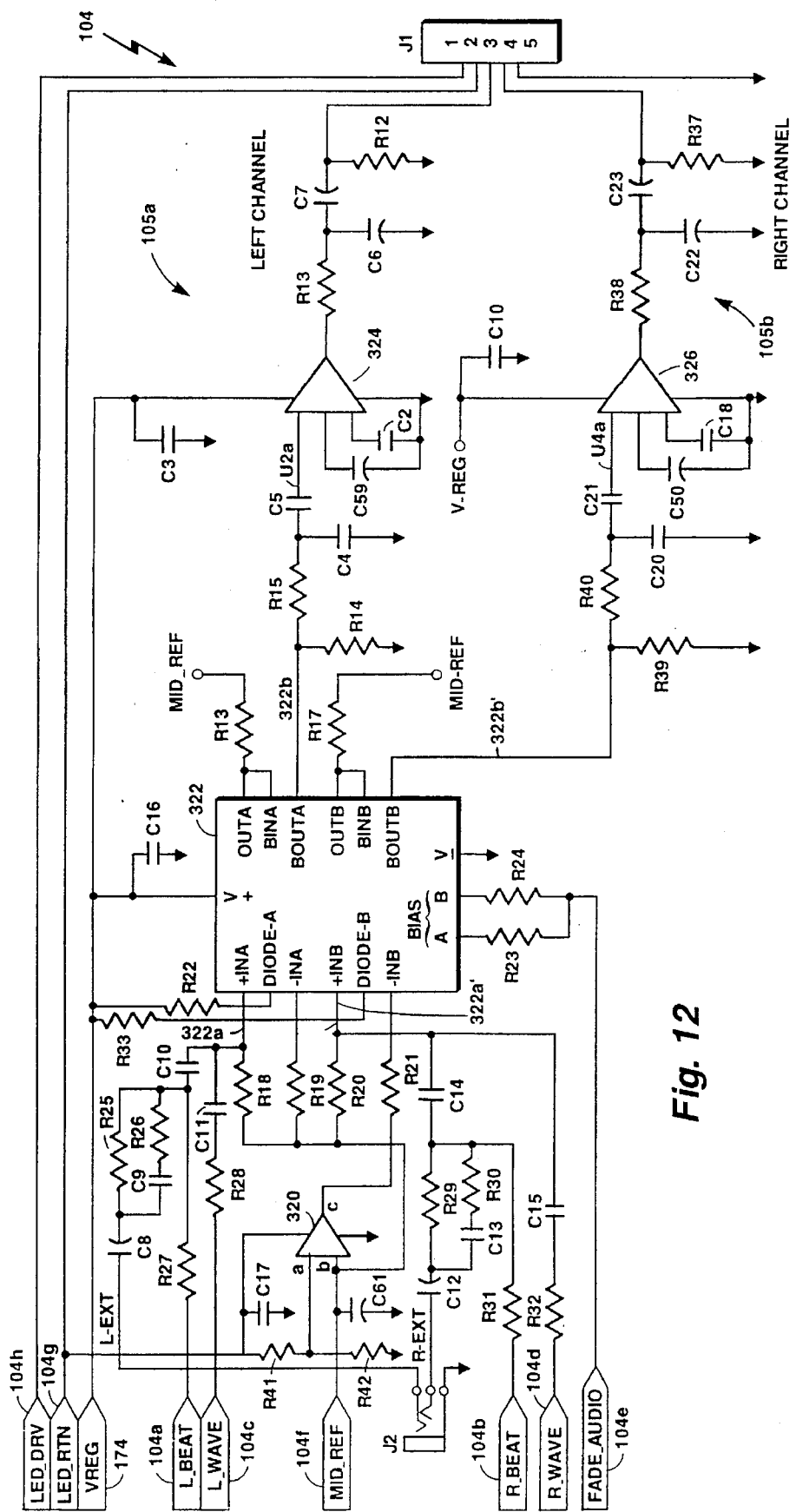
FIG. 12 is a schematic diagram of the audio portion of an embodiment of the system of FIG. 9.

The FADE_AUDIO signal at terminal 176 is coupled to audio subsystem 104 (FIGS. 10, 12) at input terminal 104e. The FADE_AUDIO signal is fed to a pair of bias ports 322a, 322b of a transconducting amplifier 322 (FIG. 12). The operation of amplifier 322 will be described further below in conjunction with FIG. 13. Suffice it here to say that as the voltage level of the FADE_AUDIO signal decreases, thus decreasing the bias voltage fed to amplifier 322, the audio signal levels provided by earphones 46 are reduced.

As will be described in conjunction with FIG. 13 below, the FADE_LED signal controls the fade-in and fade-out of LEDs 54 (FIG. 8) such that the brightness of the LEDs may be gradually increased or reduced (i.e. faded-in or faded-out) rather than simply being abruptly turned on or turned off. It should be noted, however, that the resistance of variable resistor R98 (FIG. 13) determines the absolute brightness of LEDs 54. As the voltage level of the FADE_LED signal decreases, amplifier 330 (FIG. 13) and likewise transistor Q10 (FIG. 13) are gradually turned off to respectively reduce the LED brightness levels.

Figure 11A:
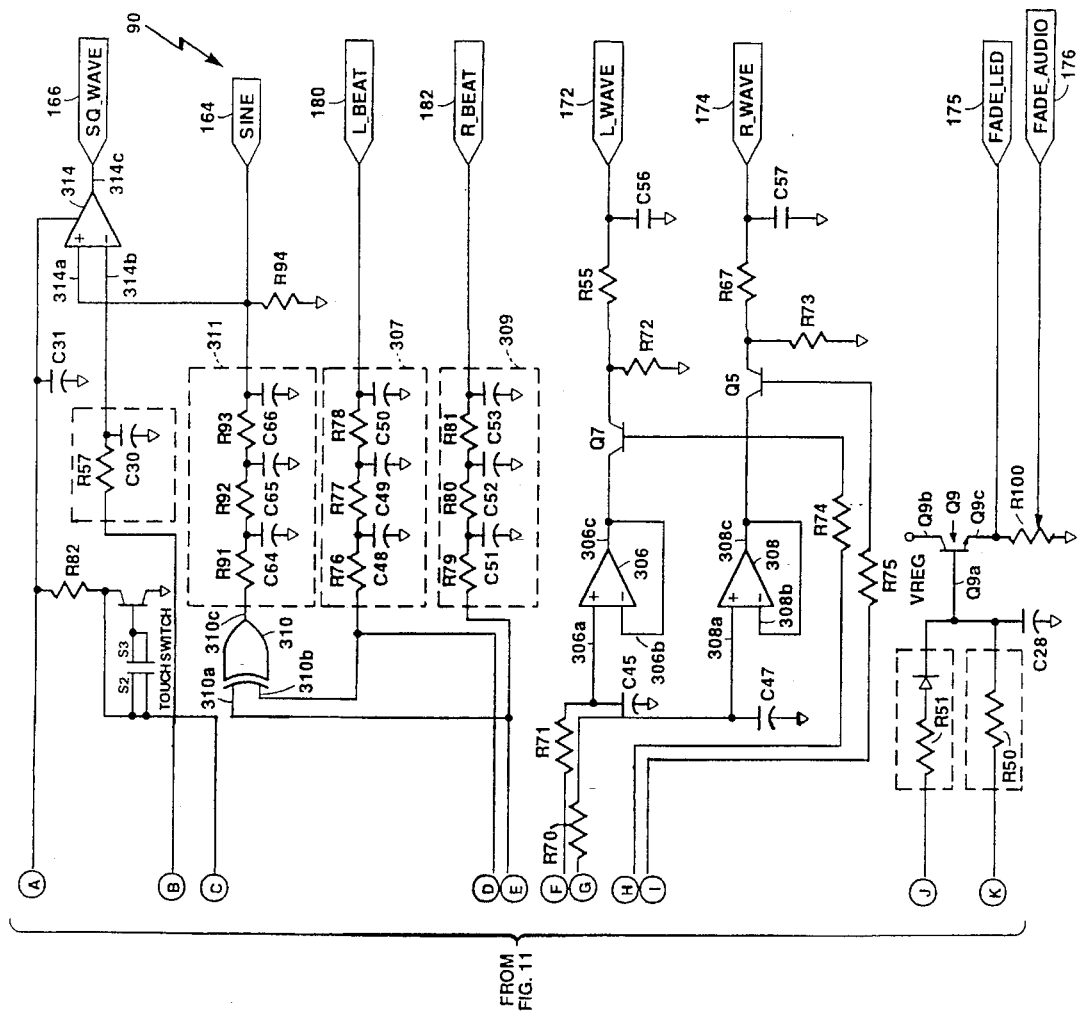

Referring now to FIG. 12, in which like elements of FIGS. 9, 10 and 11–11A are provided having like reference designations, the audio subsystem 104 described above in conjunction with FIG. 9 is here shown to include a pair of like left and right audio channels 105a, 105b, each having first and second pairs of input signal paths along which corresponding ones of the L_BEAT, L_WAVE and R_BEAT, R_WAVE signals are fed from the microprocessor system 100 (FIG. 1.2). Signals L_BEAT, L_WAVE, R_BEAT and R_WAVE are fed to a transconductance amplifier 322 at respective ones of first and second input ports 322a, 322a'. Audio circuit 104 further includes an external input port J2 to accept a stereo input jack. Thus, left and right external signals L_EXT and R_EXT may also be fed to corresponding ones of the transconductance amplifier input ports 322a, 322a'.

Such external signals may be provided, for example, from an external source such as an analog cassette tape deck, a digital audio cassette player, a compact disc player or the like. Such external signals may correspond to music or simply verbal instructions or suggestions designed to aid a user in achieving a trophotropic response.

The transconductance amplifier 322 may be provided, for example, as the type manufactured by National Semiconductor and identified as part number LM13600. Resistors R25, R27 and R28 mix the individual L_BEAT, L_WAVE and L_EXT signals in desired proportions and the signals are combined at the junction of resistor R18 and input port 322a of amplifier 322. It should also be noted that capacitor C9 and resistor R26 coupled as shown provide a treble boost to the L_EXT signal. Transconductance amplifier 322 receives the combined L_BEAT, L_WAVE and L_EXT signals and provides a corresponding output signal on a first output signal path 322b.

Similarly, resistors R29, R31 and R32 mix the individual R_EXT, R_BEAT and R_WAVE signals in desired proportions and the signals are combined at the junction of resistor R20 and input port 322a' of amplifier 322. Capacitor C13 and resistor R30 coupled as shown provide a treble boost to the R_EXT signal. Transconductance amplifier 322 combines the R_BEAT, R_WAVE and R_EXT signals and provides a corresponding output signal on a second output signal path 322b'.

The gain of amplifier 322 is set by the current through resistors R23, R24. This current is approximately proportional to the voltage of the FADE_AUDIO signal provided on input port 104e. The first and second output signals provided from amplifier 322 are fed to respective ones of a pair of amplifiers 324, 326 at input ports 324a, 326a. Amplifiers 322, 324 amplify the signals fed thereto and provide the signals having appropriate signal levels to a connector J1.

Figure 13:
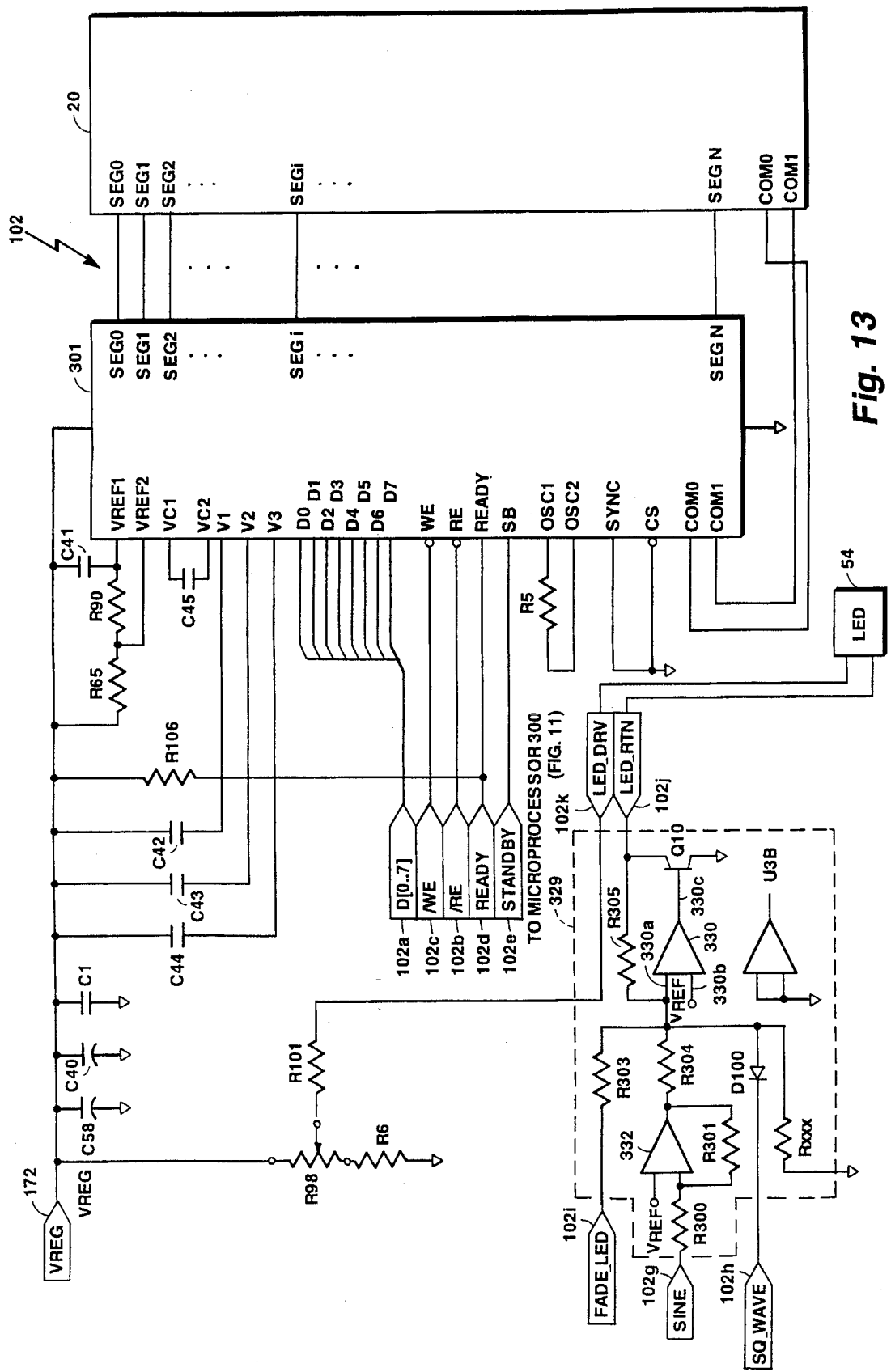
FIG. 13 is a schematic diagram of the video portion of an embodiment of the system of FIG. 9.

Referring now to FIG. 13, the display subsystem 102 includes an LCD driver circuit 301 and an LED driver circuit 329. The LCD driver circuit 301 includes a random access memory (RAM) and an internal oscillator. The LCD driver circuit 301 may be provided, for example, as the type manufactured by Hitachi and identified as part number HD61602. The LCD driver circuit 301 is coupled to the LCD display 20 and uses the internal oscillator to refresh the display of data on the LCD display 20 at a predetermined rate corresponding to the frequency of the oscillator.

The LCD driver circuit 301 receives a plurality of data input signals D0–D7 on a corresponding plurality of input data lines generally denoted 102a. LCD driver circuit 301 also receives from microcontroller 300 a plurality of control signals /WE, /RE, READY and STANDBY on control lines 102b, 102c, 102d, and 102e. When LCD driver 301 provides a READY signal on output terminal 102d, microcontroller 300 (FIG. 10) provides one or more active signals to LCD driver circuit 301 and LCD driver circuit 301 performs a corresponding function. For example, when the microcontroller 300 sends an active write command /WE to the LCD driver circuit 301, the LCD driver circuit 301 functions to display the data on lines D0–D7 on the LCD display 20. It should be noted that to display a segment, both an address and the data should be passed over the 8-bit bus. Thus two write cycles are required to display data.

The microcontroller 300 also provides SINE, SQ_WAVE, and FADE_LED signals to the LED driver circuit 329 of the display subsystem 102. The SINE and SQ_WAVE signals are coupled to the LED_DRV signal path 102R through amplifiers 330, 332.

The sinusoidal control signal SINE provided by the microcontroller 300 (FIG. 11) at output port 164 (FIG. 11A) is fed to subsystem 102 at terminal 102g and is coupled through serial resistor R300 to a first input terminal, here corresponding to a negative input terminal, of an inverting buffer amplifier 332. A second input terminal, here corresponding to a positive input terminal, of inverting buffer amplifier 332 is coupled to a reference voltage $V_{REF}$. Reference voltage $V_{REF}$ is here provided having a value corresponding to $V_{REG}/2$. When the amplitude of signal SINE at the first input terminal of amplifier 332 is greater than the amplitude of $V_{REF}$, then amplifier 332 provides an output signal having a first value. When the amplitude of signal SINE at the first input terminal of amplifier 332 is less than the amplitude of $V_{REF}$, then amplifier 332 provides an output signal having a second different value.

The output signal from amplifier 332 is fed to a difference input 330a of amplifier 330. Likewise the FADE_LED and SQ_WAVE signals are coupled to amplifier input 330a. An emitter of transistor Q10 is coupled to terminal 102j and is also coupled to amplifier input 330a through a resistor R305.

Figure 8:
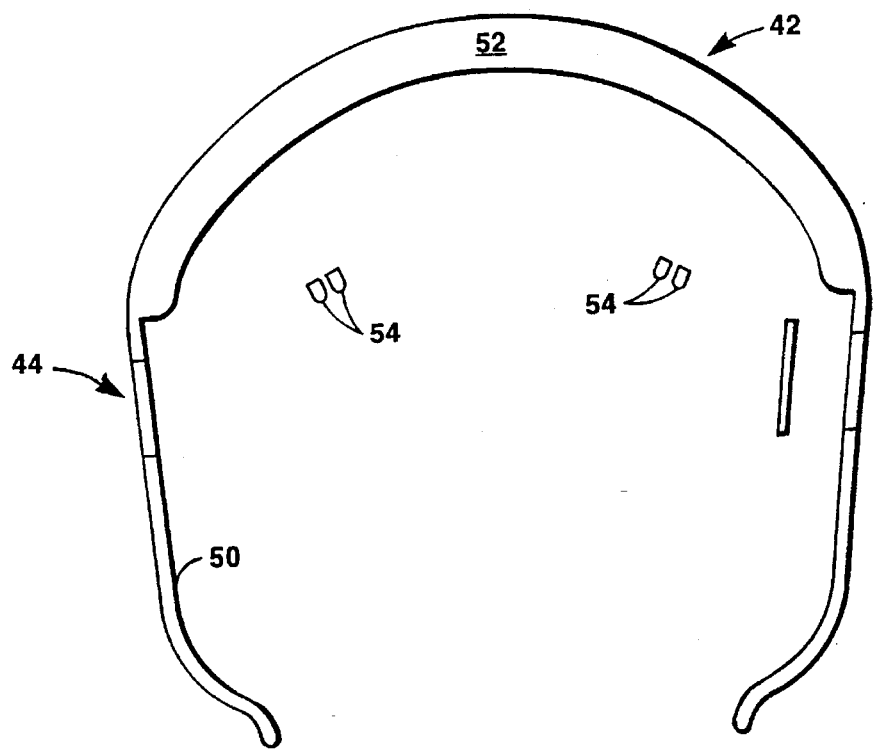
FIG. 8–8B are an exploded view of the embodiment of the audio-visual module of FIG. 7.
Figure 8B:
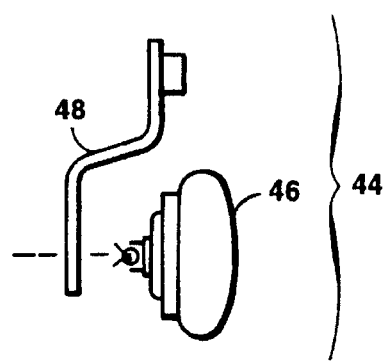
Figure 8A:
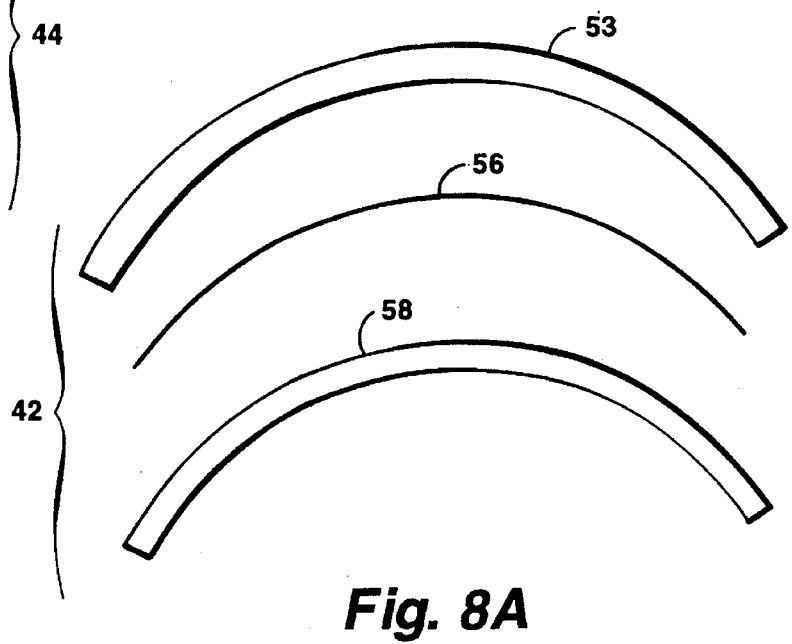

Amplifier 330 and transistor Q10 form a high current output inverting amplifier which drives LEDs 54 (FIG. 8).

The sinusoidally shaped output signal SINE from microprocessor 90 (FIG. 10) is coupled through inverting buffer amplifier 332 to the difference input 330a of driver amplifier 330. The emitter electrode of transistor Q10 is also coupled to this summing junction as is the output terminal of the square wave generator provided from amplifier 314 (FIG. 11A).

It should be noted that in this particular embodiment fade circuitry goes low to turn off LEDs 54. That is, when the signal provided at the negative input terminal 330a of amplifier 330 corresponds to a first predetermined value, transistor Q10 is biased into its conduction state and thus provides a low impedance signal path between terminal 102j and ground. When the signal provided at the negative input terminal 330a of amplifier 330 corresponds to a second predetermined value, transistor Q10 is biased into its non-conduction state and thus provides a relatively high impedance signal path between terminal 102j and ground. Thus the potential on terminal 102j alternates between first and second voltages in accordance with the conduction state of transistor Q10. This causes LEDs 54 to turn on and off in accordance with the voltage level on terminal 102j.

When driver circuit 331 provides square wave signals to the LEDs 54, the output of amplifier 330 goes low to pull the driver amplifier difference input to ground for most of the cycle (e.g., during the trough of the sine wave—which corresponds to approximately 60 to 70% of the cycle). Although a true square wave is not provided since the signal peaks are rounded, the sharp turn on and turn off of transistor Q10 provides a signal having a substantially pulse wave shape.

LEDs 54 are driven by a sinusoidal signal. The brightness of LEDs 54 periodically increase and decrease dependent upon the amplitude of the sinusoidal signal. The frequency of the sinusoidal signal may be varied in frequency from typically 3 HZ to about 30 Hz. Depending upon the particular operating mode of the system the starting frequency may vary from, for example 30 Hz to 3 Hz.

If the binaural beat frequency, and thus the light flash frequency is relatively slow, less than 11 Hz for example, then the shape of the waveform driving LEDs 54 is substantially sinusoidal. That is, the signal waveform driving LEDs 54 is smoothly varying such that LEDs 54 turn on and off relatively gradually without any abrupt increases or decreases in LED brightness. Thus LEDs 54 provide a light pattern which appears continuous to a user. This results in a preferred appearance to a user at relatively low frequencies.

If the binaural beat frequency and thus the light flash frequency is relatively fast (e.g. greater than 11 Hz), then it is desirable to drive LEDs 54 with a signal which sharply turns LEDs 54 on and off. Thus at relatively high light flash frequencies, LEDs 54 are preferably driven with a pulse waveform signal. For example, a square wave signal having a duty cycle less than 50 percent may be used.

When binaural beat frequency and thus the light flash frequency reach a predetermined value, 11 Hz for example, then rather than abruptly changing the signal waveform of the LED drive signal from a sinusoidal waveform to a pulse waveform, it is preferred to phase in the pulse wave signal and phase out the sinusoidal waveform signal. Thus, in this example, when the binaural beat frequency reaches 11 Hz and increases above 11 Hz, a pulse waveform signal is added to a portion of the sinusoidal signal corresponding to the highest portion of the sinusoidal waveform signal.

As the frequency continues to increase past 11 Hz, the amplitude of the pulse wave signal continues to increase. Furthermore, the amplitude of the sinusoidal signal may be reduced such that the pulse waveform signal characteristics dominate the sinusoidal signal characteristics. The sinusoidal signal amplitude may be reduced in a linear or any other manner such that at 20 Hz the amplitude of the sinusoidal signal is substantially zero. Thus the sharpness of the LED drive signal waveform is increased which produces a corresponding increase in the sharpness of the light pattern provided by LEDs 54.

As mentioned in the above example, the LED drive signal waveform characteristic is preferably changed from a sinusoidal waveform shape below 11 Hz to a pulse waveform shape at about 20 Hz. This selection of drive waveform shape may of course be modified to provide any desired light pattern. For example, in some applications it may be desirable to provide the LED drive having a sinusoidal waveform shape below 6 Hz and a pulse waveform shape at about 14 Hz.

Transistor Q10 increases the current drive of operational amplifier 330. This allows a proportional drive signal to be fed to LEDs 54. That is, a proportional current is fed to LEDs 54 and the LEDs 54 are not abruptly turned on and off. Thus, if the voltage level of the FADE_LED signal is increased or decreased, the brightness of LEDs 54 changes proportionately. Similarly, as the voltage level of the SINE signal increases or decreases the brightness of LEDs 54 changes proportionately. The SQUARE signal operates to effectively turn on and off the SINE signal. The FADE_LED signal works as an override signal, limiting the brightness of LEDs 54 due to the sine and square wave signals.

Figure 14:
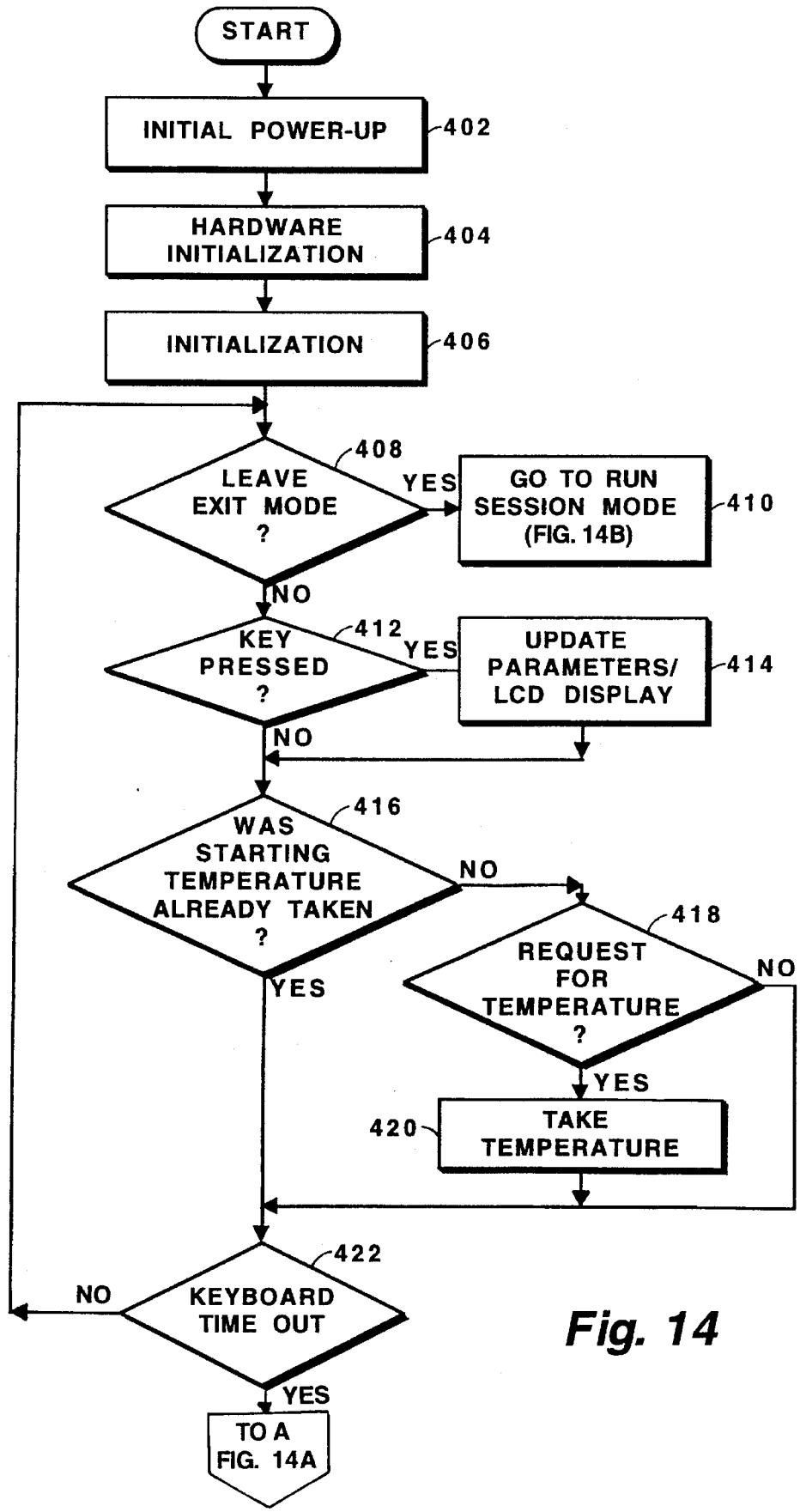
FIGS. 14–14I are a series of high level flow diagrams of the processing performed by the microcomputer subsystem of FIG. 9.
Figure 14A:
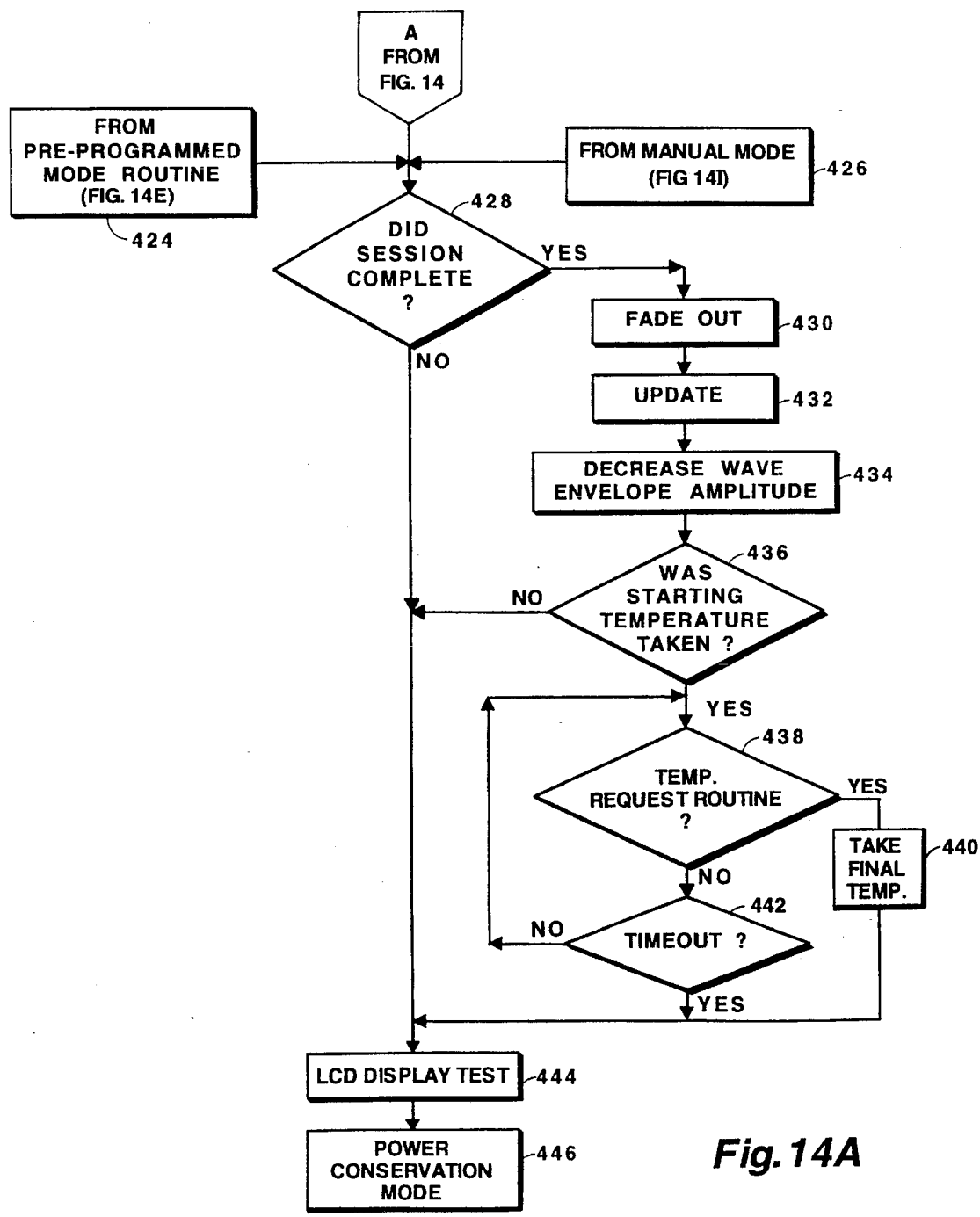
Figure 14B:
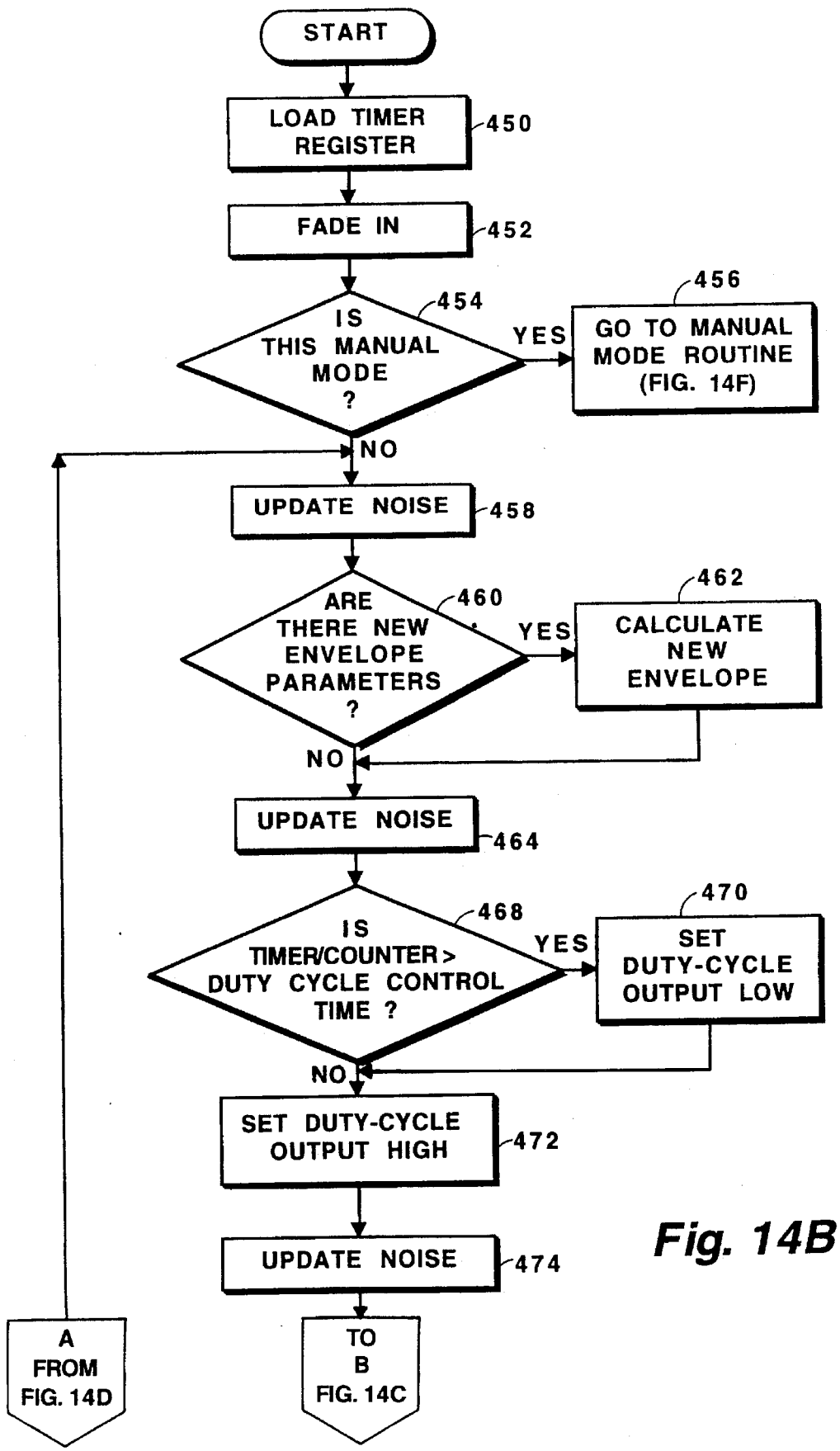
Figure 14C:
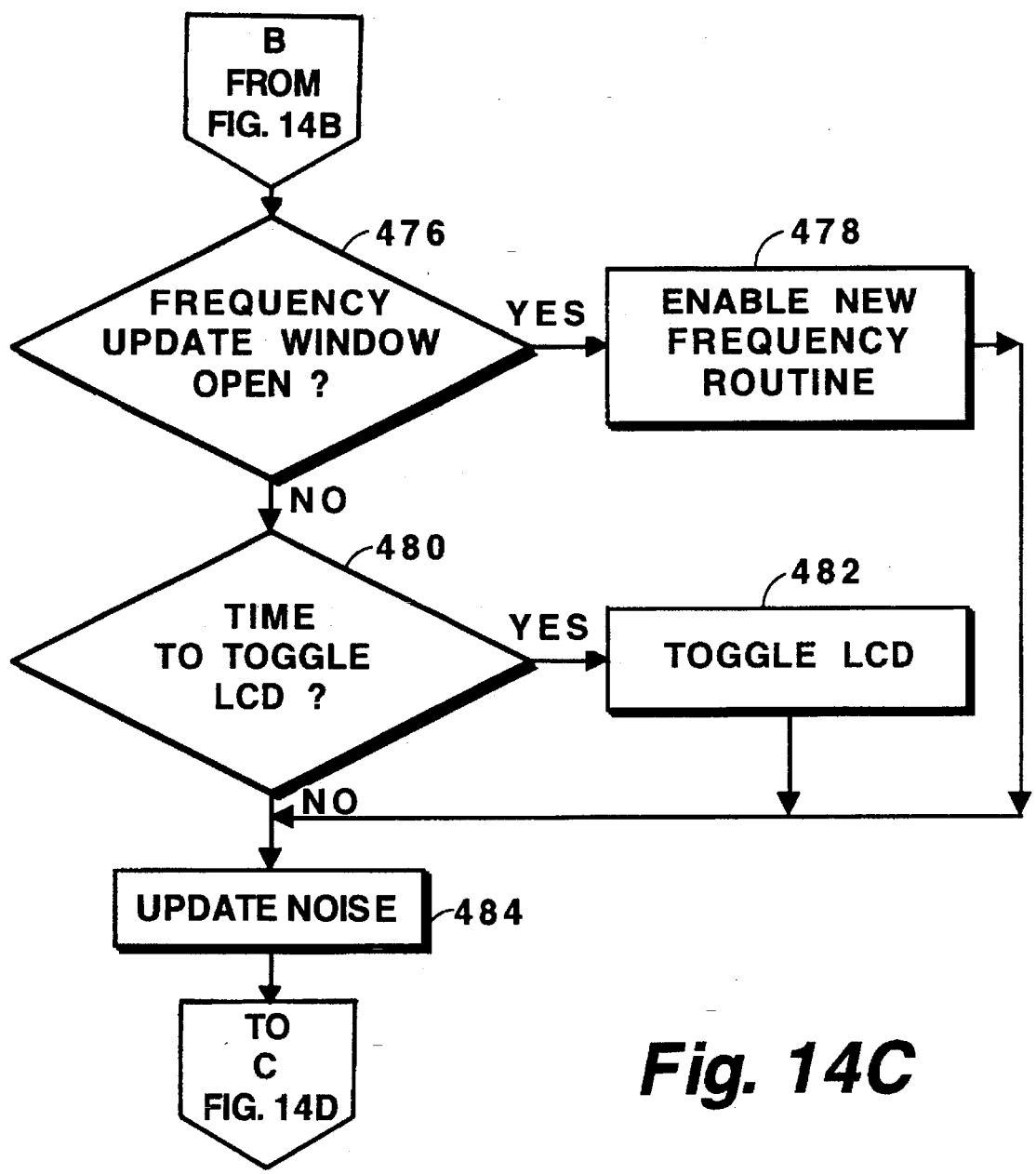
Figure 14D:
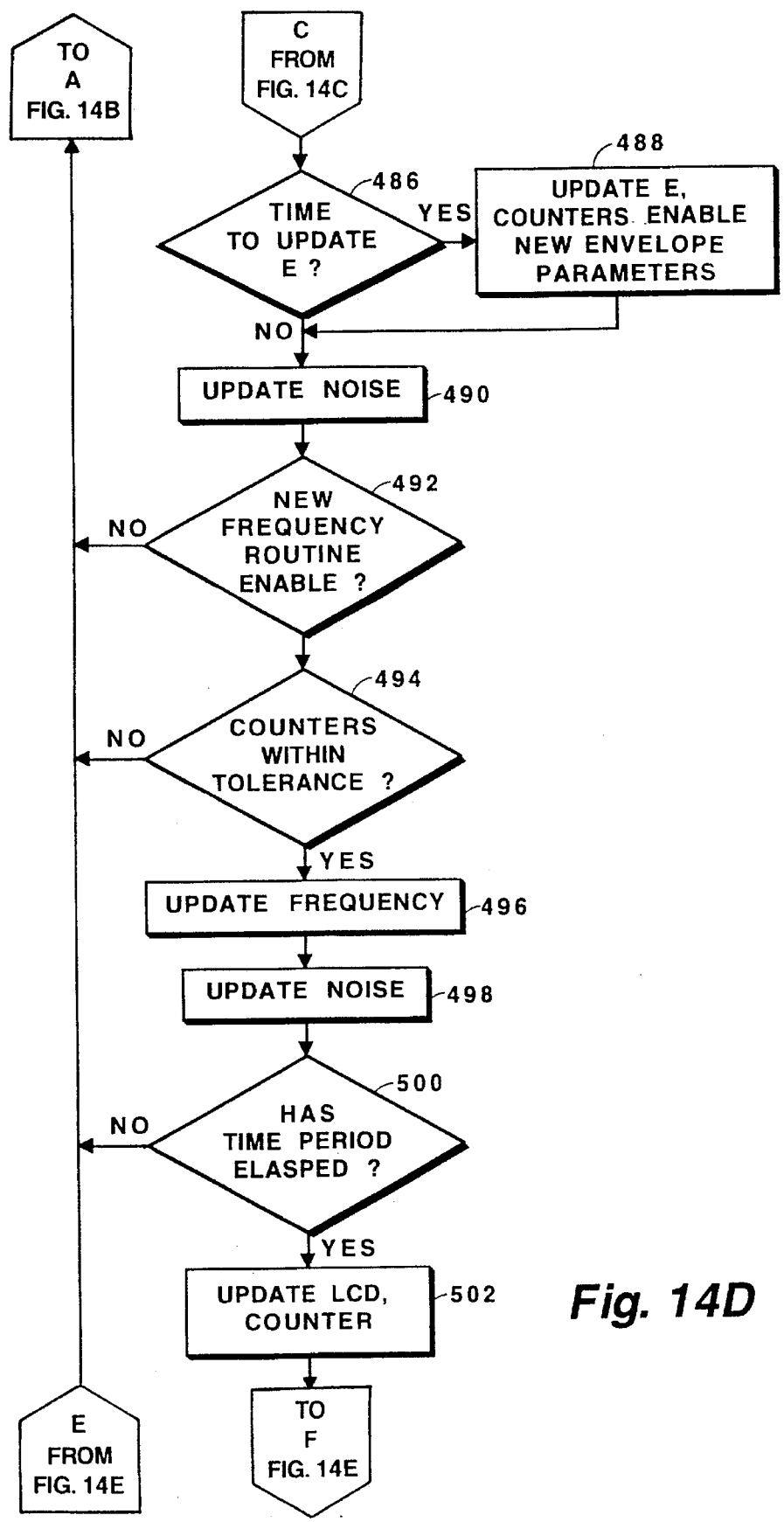
Figure 14E:
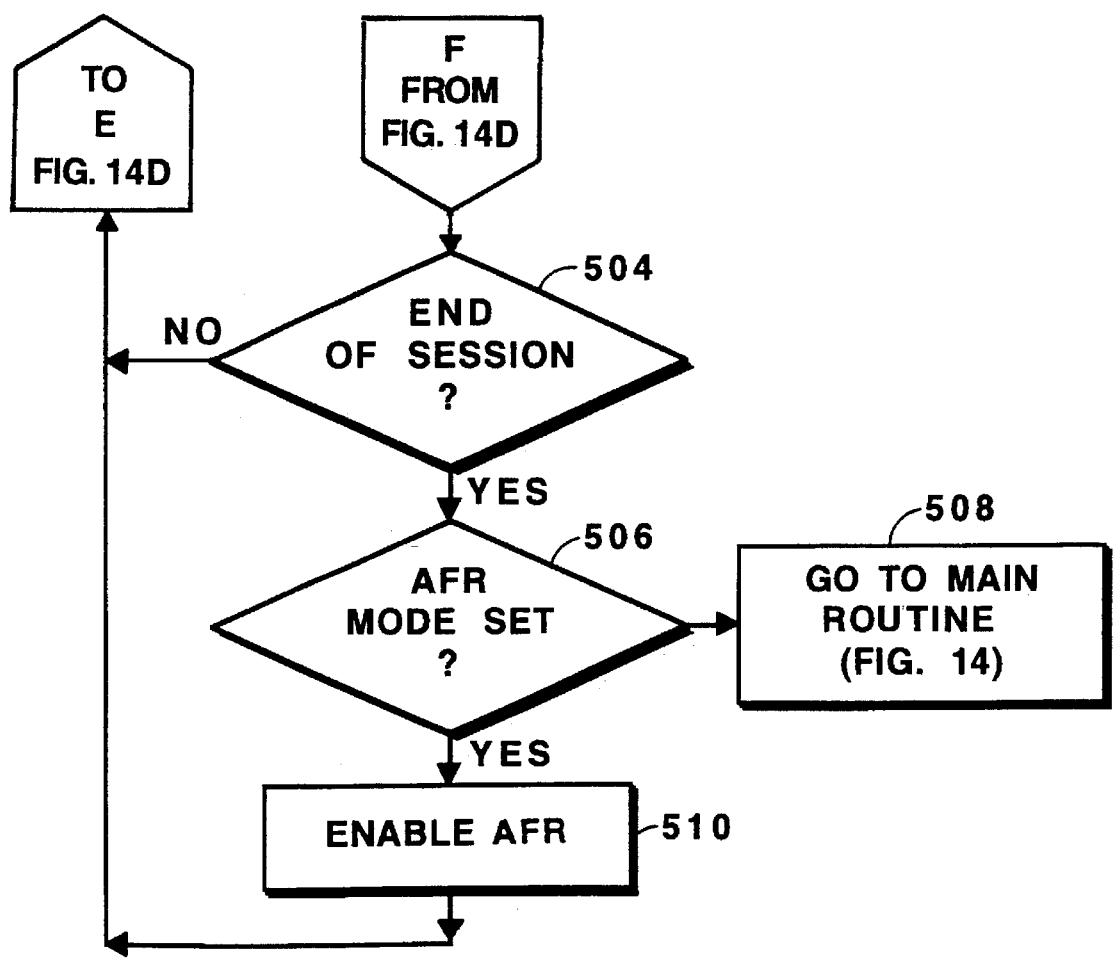
Figure 14F:
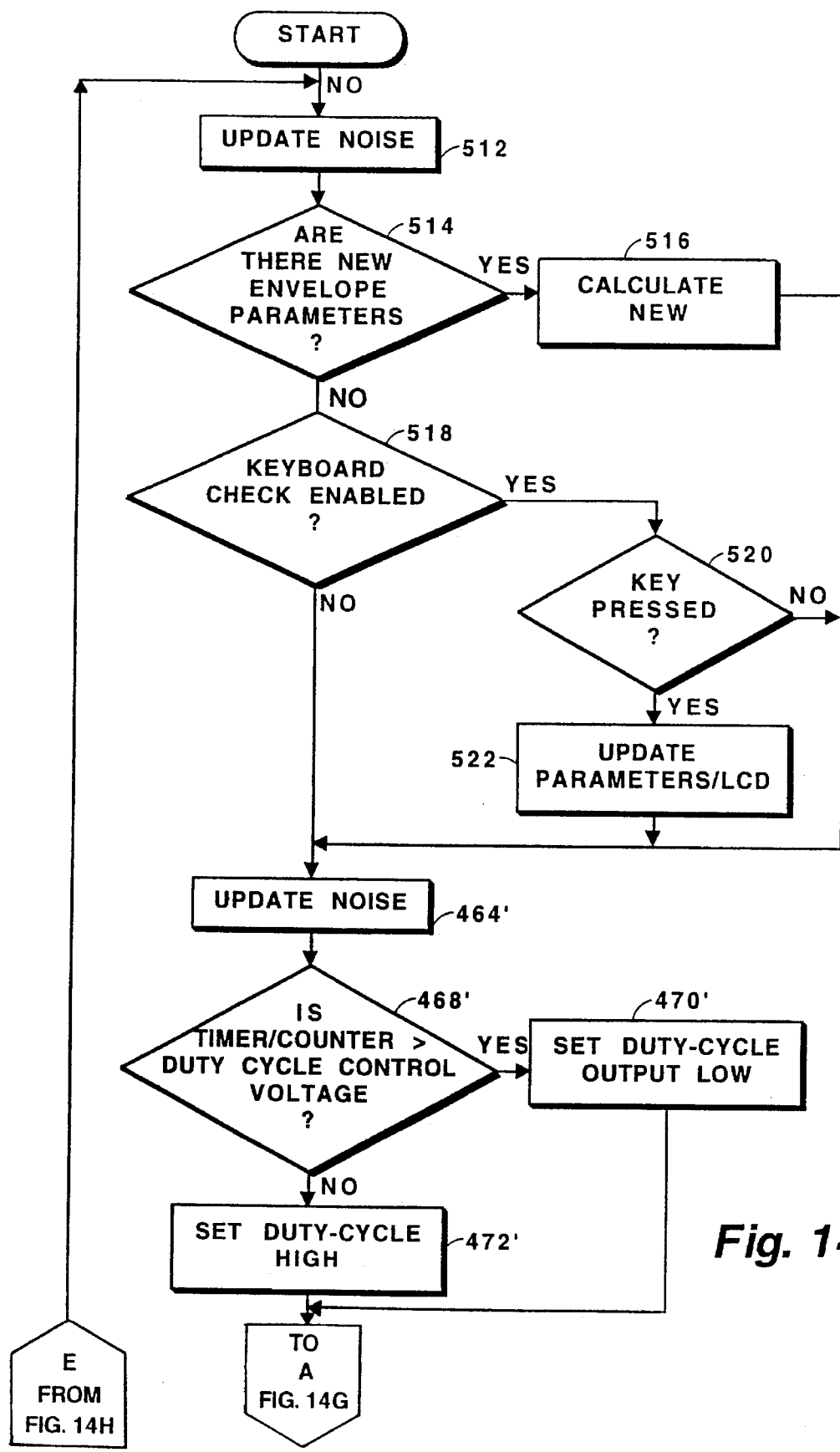
Figure 14G:
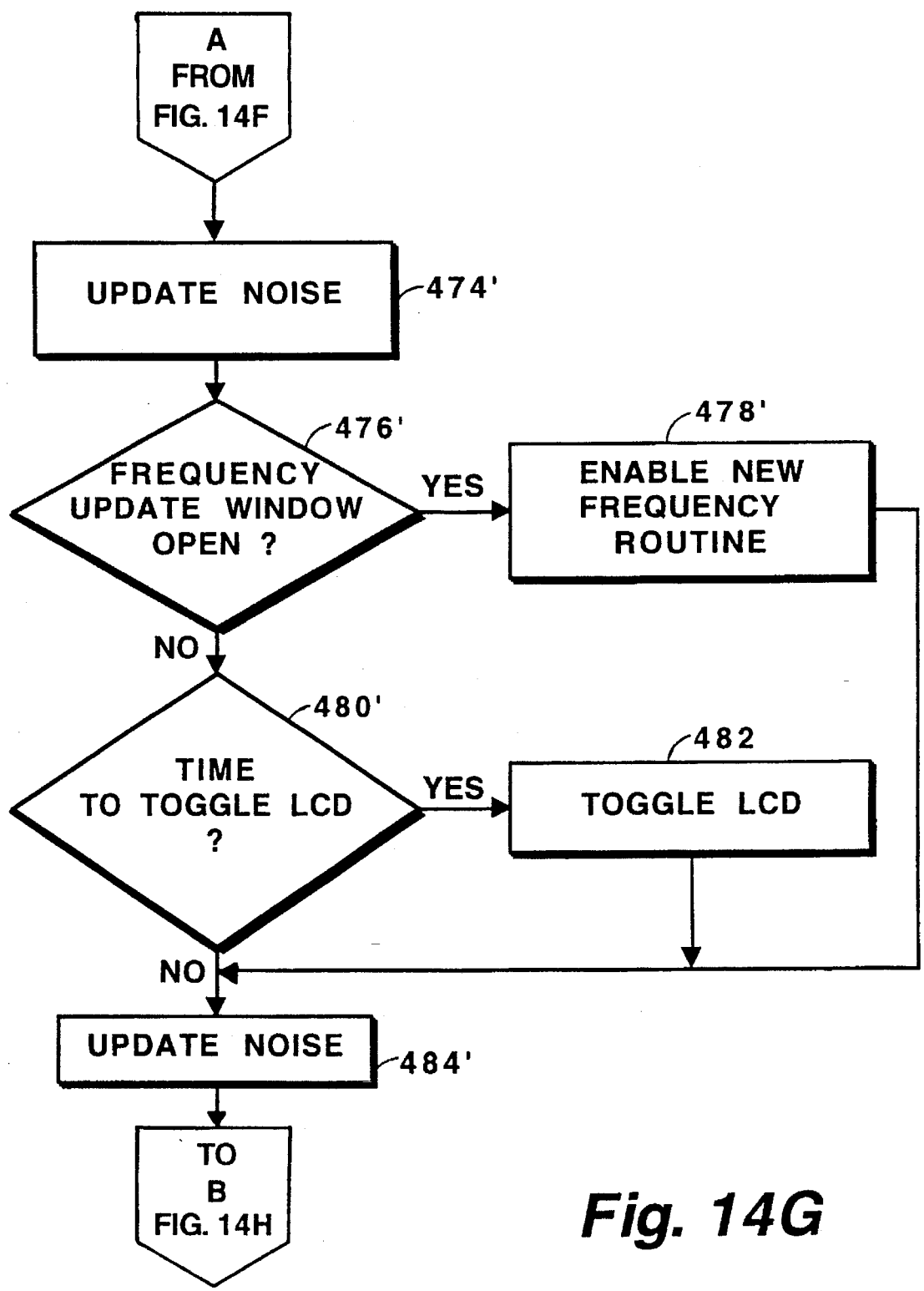
Figure 14H:
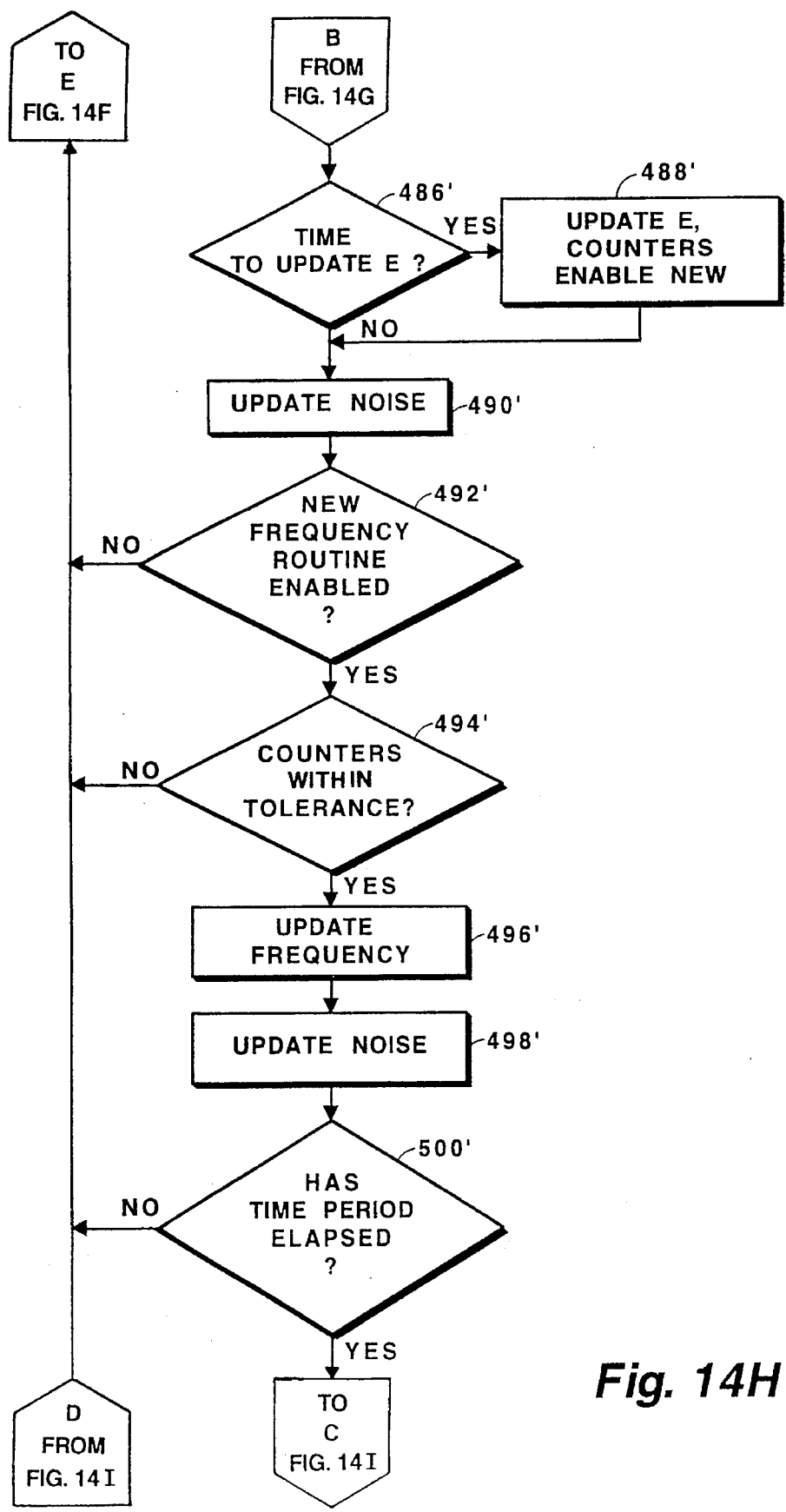
Figure 14I:
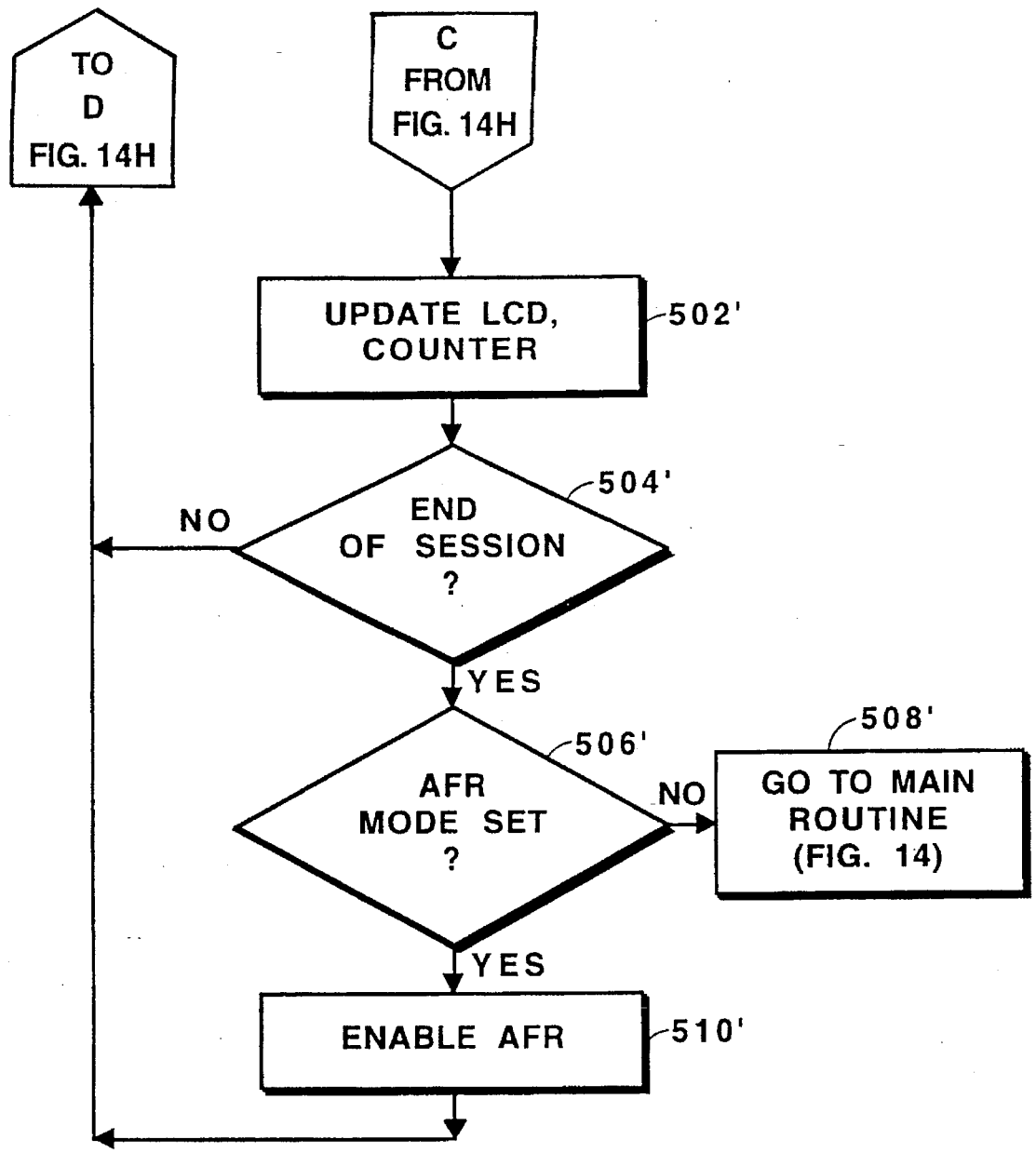

FIGS. 14–14I show a series of flow diagrams of the processing performed in the microcomputer 90 (FIG. 10) of the control module 10 (FIGS. 1–6) to provide output and control signals to the display 20 (FIG. 1) and the audio visual module 12 (FIG. 7).

In the flow diagram, the rectangular elements (typified by element 402) herein denoted "processing blocks" represent computer software instructions or groups of instructions. The diamond shaped elements (typified by element 408) herein denoted "decision blocks" represent computer software instructions or groups of instructions which affect the execution of the computer software instructions represented by the processing blocks. The flow diagram does not depict syntax or any particular computer programming language. Rather, the flow diagram illustrates the functional information one skilled in the art requires to generate computer software to perform the processing required of control module 10. It should be noted that many routine program elements such as initialization of registers, loops and variables and the use of temporary variables are not shown.

Turning now to FIG. 14, processing block 402 performs a first initialization procedure upon initial power up of the system. Initialization routine 402 is performed only once when power is initially supplied to the unit (e.g when batteries are initially placed in the unit). During the initialization procedure, parameters including but not limited to microcomputer 90 output terminals, the temperature output ports, the liquid crystal diode (LCD) display 20 and all microcomputer interrupt masks are cleared. The external interrupt mode of microprocessor 300 is enabled and the control module 10 (FIGS. 1–6) is placed in the power on mode.

In processing block 404, a second initialization procedure is performed. In the second initialization procedure the direction (i.e. inputs or outputs) of the bi-directional data ports of microprocessor 300 are set and the microprocessor registers are initialized. The second initialization procedure 404 is performed whenever the system emerges from the so-called "sleep mode" or power conservation mode. When the system emerges from sleep modes the operation of the LCD display 20 is verified and a predetermined set of information is displayed. Such information may, for example, correspond to default start and end frequencies and a default session time.

As show in processing block 406 a third initialization procedure occurs during which the keyboard is scanned and variables are set according to particular keys on the keyboard which have been actuated. Also an overflow check is performed and the current information stored in the microprocessor 300 is updated and displayed on LCD display 20.

Processing begins in the Edit Mode with decision block 408. In decision block 408, when the GO button 38 (FIG. 1) is pressed then the processing leaves the Edit Mode and flows to the Run Session mode as shown in processing block 410. The Run Session mode will be described below in detail in conjunction with FIGS. 14A–14B. Suffice it here to say that in the Run Session mode a decision is made as to whether the system will operate in a so-called Pre-programmed Mode or a Manual Mode.

Until the GO button 38 is pressed processing continues in the edit to decision block 412. In response to any key on key pad 28 (FIG. 1) being pressed program parameters and LCD display 20 are updated. If no key is pressed, processing continues to decision block 416 where a determination is made as to whether a starting temperature was taken.

The determination is made by examining a flag TEMP_DONE which is set to zero if the starting temperature of the user has not been taken and set to one if the user's starting temperature has been taken. The TEMP—DONE flag is set in response to a finger being placed on the temperature sensor 22 (FIG.1). Thus, the user's starting temperature is taken only once.

If the TEMP_DONE flag is not set, then processing continues to decision block 418 where the system determines whether a user wants to have finger temperature measured. This determination may be accomplished for example by examining a bit on input port and of microprocessor 300 which indicates whether a contact switch coupled to sensor 22 is engaged indicating that the user has placed a finger on temperature sensor 22. If there is an indication that a request for temperature has been made, then processing continues to processing block 420 where the user's finger temperature as measured by temperature sensor 22 is stored in a memory location of microprocessor 300.

Regardless of whether the starting temperature was taken, processing continues to decision block 422 where microprocessor 300 determines if a predetermined amount of time has passed without the microprocessor receiving any keyboard inputs. The predetermined amount of time may correspond for example to 120 seconds. Time periods longer or shorter than 120 seconds may of course also be used. If the predetermined period of time has passed without any keyboard inputs, then processing loops back to decision block 408 where decision is made to leave the edit mode. Every time a key is touched or a temperature is taken, the time out counter is reset to zero. When no inputs have been received and GO button 38 has not been pressed to start the session, the time out counter continues to count.

If no buttons have been pressed for a predetermined period of time then a so-called time out occurs and processing continues to decision block 428 where a determination is made as to whether a session was completed. If a session was not completed then-processing continues to processing blocks 444 and 446. In processing block 444 an LCD display test is performed. The LCD display test may include, for example, the step of flashing the LCD display twice. The LCD display test indicates that the system is about to enter a power conservation mode.

After the LCD display test, processing continues to processing block 446 in which the system enters a power conservation mode which may be referred to as a so-called "sleep mode." In the power conservation mode, microprocessor 300 terminates power to substantially all other power consuming devices such as other integrated circuits and the like. The microprocessor itself then enters a power conservation mode and but remains powered on and monitors signals provided from external inputs, interrupts and the like. It may be possible to place other devices besides microprocessor 300 in a sleep mode rather than totally removing power from the devices. If an interrupt or other input signal is received, microprocessor 300 emerges from the sleep mode and reactivates the control module circuitry and processing begins again in initialization step 404.

If in decision block 428 a decision is made that a session has completed then a fade out routine is performed as shown in processing blocks 430–434. During fade out step 430 the brightness of LEDs 54 (FIG. 8) are gradually reduced as is the sound level provided from earphone 46. In processing block 432 noise values are updated and in processing block 434 a wave envelope amplitude is decreased. The noise values and the wave envelope will be described further below in conjunction with FIGS. 14A–14I. Suffice it here to say that such signals are generated to provide an appropriate audio environment to a user.

After the fade out is complete, the system determines whether a starting temperature was taken in decision block 436. If a starting temperature was not taken then system performs the LCD display test and enters the power conservation mode as shown in steps 444 and 446. If a temperature was taken at start of session in processing block 420 then it would be desirable to compute any change in temperature which occurred as a result of completing a session since this may be an indication that a trophotropic response was achieved. Thus if a starting temperature was taken, processing continues to a temperature request routine as shown in step 438.

If a request is made to take a final temperature then a final temperature is taken as shown in step 440. A user makes a request for temperature by placing a finger on temperature sensor 22. If no request to take a final temperature is made then processing continues to decision step 442 which implements a loop to wait a predetermined period of time. If no request to take a final temperature is made within the predetermined period of time, the processing continues to the LCD display step 444 and power conservation mode step 446.

Referring now to FIG. 14A, when GO button 38 is pressed, processing flows to the Run Session mode. In the Run Session mode processing may occur in either the so-called Pre-programmed Mode or the so-called Manual mode. Manual Mode processing will be described in conjunction with FIGS. 14C–14D.

Upon entering the Run Session routine, as shown in processing block 450 microprocessor timer registers are loaded with predetermined values. Depending upon the values which the session parameters have assumed upon initial start up, a predetermined time corresponding to the time between each signal update is loaded into the timer registers. Thus for example, if a starting frequency corresponds to 20 Hz then a predetermined period of time exists between each event which must be done to maintain the frequency of 20 Hz. Thus the time between each update may be computed or looked up in a table and loaded into the timer register.

Processing then continues to processing block 452 where a fade-in routine is performed. During fade-in step 452 the audio and visual signals provided by system 9 are initially provided to the user at relatively low amplitude levels.

Processing then continues to decision block 454 where a decision is made based on whether the user is operating in manual mode. If the system is operating in manual mode then processing flows to the manual mode processing steps described in conjunction with FIGS. 14B, 14C as shown in processing block 456. If the system is not operating in manual mode then processing continues in processing block 458 where noise parameters are updated.

Processing then continues to decision block 460 where decision is made concerning the computation of new envelope values. The frequency of the binaural beat signal is changing at a predetermined rate here corresponding to a rate of 2.4 Hz/minute. Thus, a change in frequency of 0.1 Hz occurs every 2.5 seconds. Therefore, every 2.5 seconds, the system must re-calculate the timer values. Consequently, in decision block 460 a determination is made as to whether 2.5 seconds has elapsed. If decision is made to compute new envelope values, then processing flows to processing block 462 where new envelope values are computed.

As mentioned above, the trophotropic control module 10 generates signals corresponding to both aural and visual signals. The aural signal may include an ocean signal component, a binaural beat or sinusoidal signal component, and an external signal component. The visual and aural signals are related by the binaural beat frequency signal component in a manner which will be described in detail further below.

Each component of the aural signal is fed to the mixer/amplifier stage. The relative amplitudes of the aural signal components are pre-set and may be expressed as a ratio. For example, one possible amplitude ratio of binaural beat signal component to ocean signal component to external signal component may be provided as a voltage ratio 1:6:6. It should be noted of course that the amplitude of the external signal may be adjusted independently of the binaural beat and ocean signal components.

Other ratios may of course also be used. In general, however, the ocean signal component is preferably selected having an amplitude greater than the amplitude of the binaural beat signal component such that the binaural beat signal component may not be an easily identifiable portion of the aural signal. Similar considerations are used when selecting the relative amplitude of an external signal component which may optionally be used. The particular relative amplitudes of the binaural beat signal, ocean signal and external signal components may be selected in accordance with a variety of factors including but not limited to the personal preference of a particular user.

The binaural beat signal is typically provided as a sinusoidal signal fed to each channel of the mixer/amplifier circuit. The frequency of the binaural beat signal varies dependent upon which audio channel the binaural beat frequency signal is fed to.

For example, the binaural beat signal fed to a first audio channel for example the left audio channel may be provided having a fixed frequency generally in the range of about 50–150 Hz. However, the binaural beat signal fed to a second different audio channel, for example the right audio channel, may be provided having a frequency which varies such that the frequency of the right side binaural beat signal corresponds to the left channel frequency plus the binaural beat frequency.

The binaural beat signals should be provided having a harmonic content such that the third harmonic is provided having a signal level less than or equal to 5% of the power level of the fundamental frequency signal, the fifth harmonic is provided having a signal level less than or equal to 13% of the power level of the fundamental frequency signal and all higher harmonics are provided having signal power levels less than or equal to 1% of the signal power of the fundamental frequency signal.

The aural signal further includes a so-called ocean signal component which may be provided for example as a random noise signal with a spectrum level having a negative slope of 10 decibels per decade generally referred to as pink noise. The pink noise signal is modulated through a pair of so-called envelope signals as will be described further below. Suffice it here to say that the pink noise in each channel is generated separately but is provided having the substantially equal amplitudes which may be computed according to Equations 1 and 2 below.

Left Channel Amplitude=$[D*(E-½)+½]*N$(left)     Equation 1

Right Channel Amplitude=$[D*(½-E)+½]*N$(right)     Equation 2 in which:

E corresponds to a value of a periodic signal having a triangular wave shape and having a minimum value and a maximum value wherein the triangle wave is generated in a triangular wave generator in the microprocessor;

D corresponds to a value of a periodic signal having a triangular wave shape and having a minimum value and a maximum value wherein the triangle wave is generated in a triangular wave generator in the microprocessor;

N(left) corresponds to the left channel pink noise amplitude; and

N(right) corresponds to the right channel pink noise amplitude.

Equations 1 and 2 show the relation between the time dependent loudness on the left channel and the time dependent loudness on the right channel. The terms N(left) and N(right) give the ocean wave sound a sense of direction which appears to move left and right in space.

E and D are variables having values in some discrete range. The portion of the equations 1 and 2 corresponding to the terms $[D*(E-½)+½]$ and $[D*(½-E)+½]$ respectively may be calculated inside the microcontroller and provide the left and right channel amplitudes. After computing the value, the microcontroller provides a corresponding analog signal for each of the left and right channels on output ports of the D/A converter (DAC). The analog signals provided by the DAC have voltage levels corresponding to the respective computed values and may for example, be in the range from 0 volts to 5 volts. Thus, the terms $[D*(E-½)+½]$ and $[D*(½-E)+½]$ determine the overall loudness of the ocean wave signal and the direction in which the ocean wave signal appears to move in.

It should be noted that the terms N(left) and N(right) correspond to noise signals and are provided having values of logic 1 or 0 to thus rapidly turn the left and right channel amplitudes on and off.

The terms $[D*(E-\frac{1}{2})+\frac{1}{2}]$ and $[D*(\frac{1}{2}-E)+\frac{1}{2}]$ provide values which modulate the N(left) and N(right) values. That is, the values computed by the terms set an envelope on the N(left) and N(right) audio noise signals.

The terms $[D*(E-\frac{1}{2})+\frac{1}{2}]$ and $[D*(\frac{1}{2}-E)+\frac{1}{2}]$ provide complementary loudness values that modulate the left and right sound and this gives the apparent ocean wave direction. E has a faster period and drives the ocean waves. That is, as E varies over a complete cycle the user hears the ocean sound coming towards him and then hears the sound recede. Where this happens in the cycle depends on the value of D.

The function of D is to slowly rotate the overall ocean wave sound. That is a user may, for example, hear ocean waves which appear to originate from the user's left and after a predetermined period of time the ocean waves appear to originate from the user's center and after another predetermined amount of time the waves appear to come from the user's right. Thus, for some values of D the ocean waves appear on the left side and move toward the right as the sound increase. The ocean waves then recede back toward the right. For other values of D the ocean waves appear to come from the right side of the user, move toward the user's left and then recede back to the right.

For example, when E assumes its minimum value then the sum of loudness (Left Channel Amplitude+Right Channel Amplitude) is generally at its lowest value. On the other hand when E assumes its maximum value then the sum of the loudness (Left Channel Amplitude+Right Channel Amplitude) is generally at its highest value. The convolution of D and E is such that sum of D and E affects balance between the left and right audio channels. That is, if D and E sum to one value then the balance is mostly left. However, if D and E sum to a second, different value then the balance is mostly right.

For example, if the sum of D and E is positive then the balance between the left and right channels may be biased substantially to the left. If sum of D and E is negative then the balance between the left and right channels may be biased substantially to the right. Consequently, because D is slowly varying and thus is approximately constant through a single ocean wave and because the ocean wave loudness generally increases as the value of E increases, a user may hear the ocean wave come in from the left and move toward the right as E assumes larger values. As the value of E decreases, the user hears the ocean wave get softer and hears the ocean wave receding back toward the left because the sum of D and E is about the same as when E started out at its minimum value at the beginning of the wave, increased to its maximum value and returned to its minimum value at the end of the wave. That is, since the value of D does not change substantially then E has a greater impact.

As D slowly changes to a new value, that will change how this wave affects the left/right balance. That is, the ocean wave sound will eventually appear to come from the right side and move toward the left and then recede back toward the right side. Thus one of the signals (E) controls the overall instantaneous loudness (i.e. the loudness of the sum of the two signals) and the other signal (D) as the slowly varying parameter, controls the way in which E affects left right balance. Thus, the value of D determines whether a loud sound should appear to come from the user's left side and soft sound toward the user's right side or vice-versa.

The D waveform may be provided having a period of about 100 or 200 seconds. The E waveform corresponds to the individual ocean waves and has a faster period than D.

Here, E and D are each provided as triangle waves. However, it should be noted that E and D may also be provided having a sinusoidal wave shape. It has been found however that triangle wave shapes give a preferred sound. It should also be noted that the period of triangle wave E can be set to vary with the frequency of the binaural beat signal.

As mentioned above, the first envelope designated "E" may be provided, for example, having a triangular waveform shape and having a signal period which varies linearly in accordance with the frequency of the binaural beat signal. For example, if the binaural beat signal frequency corresponds to 20 Hz, the period of the first envelope signal E should correspond to about 6 seconds. Alternatively, when the frequency of the binaural beat signal is 1 Hz, the period of the first envelope signal E should correspond to about 12 seconds.

The values of 6 and 12 seconds were empirically determined. In general, however, the period of the ocean wave signal is selected to be shorter at high light flash frequencies. This selection is made because user excitation should be occurring at higher light flash frequencies. User relaxation, on the other hand, should be occurring at the lower light flash frequencies. Thus at the lower light flash frequencies, the ocean wave period should be somewhat longer than the ocean wave period at the higher light flash frequencies.

Thus, the first envelope signal "E" is provided having a triangular waveshape and a value typically in the range of about a minimum value 0.05 and a maximum value of about 1.0. The second envelope signal "D" may also be provided having a triangular wave shape and may be provided having a period typically of about 100 seconds and maximum and minimum values respectively typically in the range of about −0.8 to +0.8.

The aural signal may also include a signal component provided from an external source. The external source may correspond for example to a user specified stereo audio input having a preset gain which may be fed directly to the mixer on the audio system. The relative volume of the external input may be controlled at the source of the external input.

The binaural beat frequency initially corresponds to a start frequency which may be provided as a default value or may be a value provided by the user. The frequency of the binaural beat signal changes at a predetermined rate which may, for example, correspond to a change of 2.4 Hz/minute until the binaural beat signal component frequency reaches an end frequency, which may also be provided either as a default value or as a value set by the user. Once the end frequency is reached, the frequency of the binaural beat signal remains constant.

The binaural beat frequency changes with a frequency step which typically is less than or equal to 0.1 Hz. The frequency step is selected such that the microprocessor provides a smooth sound. Those of ordinary skill in the art will recognize of course that other frequency steps may also be used.

The visual signal may be provided having any amplitude between first and second predetermined amplitude values. Thus the visual signal may be provided having any amplitude value between 0 and 100% of a predetermined maximum signal amplitude. The amount of light provided by the LEDs 54 will depend of course on the particular type of LEDs which are used.

The visual signal may be provided having a frequency which corresponds to a multiple of the frequency of the binaural beat signal. In a preferred embodiment, the visual signal is provided having a frequency which equals the frequency of the binaural beat signal.

The visual signal may be provided having a plurality of signal components. For example, the visual signal may be provided from a sinusoidal signal fed through a filter having a low pass filter characteristic with a 3 decibel (dB) cutoff frequency typically of about 8 Hz and a pulse wave having a predetermined duty cycle and an amplitude which changes linearly between a first predetermined frequency to a second predetermined frequency. In a preferred embodiment, for example, the pulse wave may be provided having a 20% duty cycle and an amplitude which increases from a predetermined minimum value below 9 Hz to a predetermined maximum value at 20 Hz and above.

For example, below 4 Hz, the LEDs can be driven with a pure sine wave. Between 9 and 20 Hz, the pulse wave duty cycle changes gradually. Above 20 Hz, the duty cycle remains steady. The sine wave amplitude diminishes as the frequency increases due to damping by the low-pass filter. Thus the pulse wave becomes a greater component of the signal as frequency increases.

Alternatively, the pulse wave may be provided having a 20% duty cycle and an amplitude which decreases from a predetermined maximum value below 9 Hz to a predetermined minimum value at 20 Hz and above. Alternatively still the pulse wave signal may be provided having a predetermined amplitude and a duty cycle which increases from 0% at frequencies below 9 Hz to 20% at frequencies of 20 Hz and above. Or alternatively still, the pulse wave signal may be provided having a constant amplitude and a duty cycle which decreases linearly from 20% at frequencies below 9 Hz to 0% at frequencies of 20 Hz and above.

The first envelope signal E is updated by a FREQ_FUNCTION, which updates envelop signal E every 0.1 Hertz (Hz). The updated envelop signal results in a new change for the BEAT frequency. Similarly, the second envelop signal D is set with the counter-overflow in the TIME_OV function. Thus the second envelop signal D is updated every time the counter produces an overflow. In this embodiment, an overflow occurs every 131 milliseconds (64K2 microseconds). Processing then continues to processing block 442 where noise values are computed and updated.

If in decision block 460 decision is made not to compute new envelope values, then the program flows directly to processing block 464 where noise values are updated.

Processing then continues to decision step 468 where the value of the timer/counter is compared With the duty cycle control time. If the timer/counter value is greater than the duty cycle control time then as shown in processing block 470 the duty cycle output signal is set low. If the timer/counter value is less than the duty cycle control time then the duty cycle output signal is set high as shown in processing block 472. As described above in conjunction with FIG. 11 a square wave signal is generated from a sinusoidal signal. Thus, the input signal CV_COMP fed to comparator 314 (FIG. 11A) is toggled between the high and low states to create a square wave output signal at comparator output port 314c.

The CV_COMP signal is toggled via a free running counter in microprocessor 300. The free running counter here has a cycle time of 130 milli-seconds (msecs). Thus, if the timer is set at 65 msec, for example, then if less than 65 msec has elapsed the duty cycle output signal is set low. If more than 65 msec has elapsed then duty cycle output signal is set high. Thus, in this example, a signal having a 50% duty cycle is provided.

Processing then continues to processing block 474 where the noise values are updated and on to decision block 476 where it is determined whether the frequency update window is open. The frequencies are updated periodically. Thus, after a predetermined amount of time has elapsed the frequencies should be updated.

A time "window" about this predetermined time period may be selected. Within this frequency update window the new frequency routine may be enabled. The window of time may correspond to the predetermined time period plus or minus 0.1 seconds. Thus, when decision block 476 is processed if an elapsed period of time within 0.1 seconds of the predetermined period of time has occurred, then processing continues to processing block 478 where the new frequency routine is enabled. Processing then flows to processing block 484 where the noise values are updated.

If the frequency update window is not open then processing flows from decision block 476 to decision block 480 where the elapsed time is compared to a time to toggle the liquid crystal diode display. If it is time to toggle the LCD display then processing continues to processing block 482 where the LCD display is toggled and processing then flows to processing block 484 where the noise values are updated. The LCD display is toggled after a predetermined period of time has elapsed. For example, the LCD toggle may occur every 0.5 seconds. Other predetermined periods of time may also be used. Processing then continues to decision block 486 where a decision is made as to whether the envelope E value should be updated. As describe above, one of the components of the computed envelope is designated E. Since E is a component of the envelope, when E changes the envelope changes. It takes a relatively large period of time to calculate the new envelope. At this particular processing point however, the processor does not typically have sufficient time to perform the calculations due to other actions being performed. Thus rather than calculating the envelope at that particular moment in time, the system is enabled to perform a new calculation.

The new envelope is calculated when the processor has time to make such a new calculation. Thus in step 460 when a determination is made if there are new parameters, the answer will be yes and at that point in time the processor has time to make the calculations.

If decision is made in step 486 to update E then processing continues to processing block 488 where the E value is updated, counters are updated and the new envelope parameter is enabled. If decision is made not to update E then processing flows to processing block 490 where the noise is updated.

In decision block 492 if the new frequency routine is enabled then processing flows to decision block 494. If the new frequency routine is not enabled then processing flows back to processing block 458 and noise values are updated.

In decision block 494 a decision is made as to whether the counters are within a predetermined tolerance value. If the counters are within tolerance then processing flows to processing block 496 where frequency values are updated and noise values are updated as shown in processing block 498. If in decision block 494 counters are not within tolerance then processing again flows back to processing block 458. After updating noise values as shown in processing block 498, processing continues to decision block 500 where decision is made as to whether a predetermined period of time has elapsed. The predetermined period of time may be selected to be five minutes for example, of course, other time periods may also be used. If the predetermined period of time has elapsed then processing continues to processing block where the liquid crystal diode display and counter are updated. If the predetermined period of time has not elapsed then processing flows back to processing block 458. In decision block 504 decision is made as to whether a session has completed. If a session has completed, then processing continues to decision block 506 where decision is made as to whether the "AFR" mode is set. If the AFR mode is not set then processing continues to the main routine as shown in processing block 508. If however, the AFR mode is set then the AFR mode is enabled as shown in processing block 510 and processing returns to processing block 458. By setting the AFR mode, regardless of the end frequency which is selected, the session continues for an additional predetermined period of time during which the light and sound frequencies are set to predetermined levels. For example the light and sound may be set to frequencies, such as 13 Hz for example, which provide an environment in which a user enters an awakened state.

Referring now to FIGS. 14E and 14F, processing steps in the manual mode are shown. Steps in Manual Mode processing are similar to Pre-programmed Mode processing steps. In the Manual Mode however, noise signals are updated as shown in processing block 512 and then a decision is made as to whether new envelope parameters exist as shown in decision block 514.

If new envelope parameters exist then a new envelop is calculate in step 516 and processing then continues to step 464' where noise values are updated. Processing then flows to steps 468'–510' which are substantially the same as steps 468–510 described in conjunction with FIGS. 14a, 14B above.

If new envelope parameters do not exist then processing flows to step 518 where it is determined whether the keyboard has been enabled. If the keyboard has been enabled then a determination is made as to whether a key has been pressed as shown in step 520. In manual mode no starting and ending frequencies exist as in pre-programmed session. Rather in manual mode only a default starting frequency exists. The user may select and change the frequencies of the visual and audio signals during the session by entering values from the keyboard. Thus, if a key has been pressed then LCD and parameters are updated as shown in step 522 and the program flows to steps 464'–510'. If a key has not been pressed then step 522 is omitted. Processing then flows to steps 468'–510' as described above.

Having described preferred embodiments of the invention, it will now become apparent to one of skill in the art that other embodiments incorporating the concepts may be used. It is felt, therefore, that these embodiments should not be limited to disclosed embodiments but rather should be limited only by the spirit and scope of the appended claims.

We claim:

1. A method for generating a signal in a relaxation response system, the method comprising the steps of:

generating a noise signal;

computing a first digital value of a first periodic signal having a first predetermined wave shape, a first predetermined period and having a predetermined minimum value and a predetermined maximum value wherein the first digital value is designated E;

computing a second digital value of a second periodic signal having a second predetermined wave shape, a second predetermined period and having a predetermined minimum value and a predetermined maximum value wherein the second digital value is designated D;

providing a modulated digital value by modulating the noise signal by a combined signal provided by combining the values D and E according to the equation $D*(E-\frac{1}{2})+\frac{1}{2}$; and converting the modulated digital value to an analog signal in a digital to analog converter.

2. A method for generating a signal in a relaxation response system, the method comprising the steps of:

generating a noise signal;

computing a first digital value of a first periodic signal having a first predetermined wave shape, a first predetermined period and having a predetermined minimum value and a predetermined maximum value wherein the first digital value is designated E;

computing a second digital value of a second periodic signal having a second predetermined wave shape, a second predetermined period and having a predetermined minimum value and a predetermined maximum value wherein the second digital value is designated D;

providing a modulated digital value by modulating the noise signal by a combined signal provided by combining the values D and E according to the equation $D*(\frac{1}{2}-E)+\frac{1}{2}$; and converting the modulated digital value to an analog signal in a digital to analog converter.

3. A method for generating a signal in a relaxation response system, the method comprising the steps of:

(a) generating a first signal comprising the steps of:
      generating a first noise signal;
      computing a first digital value corresponding to a value of a first periodic signal having a first predetermined wave shape, a first predetermined period and having a predetermined minimum value and a predetermined maximum value;
      computing a second digital value corresponding to a value of a second periodic signal having a second predetermined wave shape, a second predetermined period and having a predetermined minimum value and a predetermined maximum value;
      providing a first modulated digital value by modulating the noise signal by the first and second digital values; and
      converting the first modulated digital value to an analog signal in a digital to analog converter;

(b) generating a second signal comprising the steps of:
      generating a second noise signal;
      computing a third digital value corresponding to a value of a third periodic signal having a third predetermined wave shape, a third predetermined period and having a predetermined minimum value and a predetermined maximum value;
      computing a fourth digital value corresponding to a value of a fourth periodic signal having a fourth predetermined wave shape, a fourth predetermined period and having a predetermined minimum value and a predetermined maximum value;
      providing a second modulated digital value by modulating the second noise signal by the third and fourth digital values; and
      converting the second modulated digital value to an analog signal in a digital to analog converter.

4. The method of claim 3 wherein the first and third wave shapes are the same.

5. The method of claim 4 wherein the first and third digital values are the same.

6. The method of claim 5 wherein the second and fourth wave shapes are the same.

7. The method of claim 6 wherein the second and fourth digital values are the same.

8. The method of claim 7 wherein the first, second, third and fourth wave shapes are triangle wave shapes.

9. The method of claim 8 wherein the periods of the first and third periodic signals are shorter than the periods of the second and fourth periodic signals.

10. The method of claim 9 wherein the first digital value is designated E, the second digital value is designated D, and the value of the first noise signal is designated $N_l$ and the value of the first signal is provided according to the equation $[D*(E-½)+½]*N_l$.

11. The method of claim 10 wherein the third digital value is designated E, the fourth digital value is designated D and the second noise signal is designated $N_2$ and the value of the second signal is provided according to the equation $[D*(½-E)+½]*N_2$.

* * * * *